United States Patent [19]

Taylor et al.

[11] Patent Number: 4,537,886
[45] Date of Patent: Aug. 27, 1985

[54] β-LACTAM ANTIBACTERIAL AGENTS AND COMPOSITIONS CONTAINING THEM

[75] Inventors: Andrew W. Taylor, Reigate; Richard T. Cook, Redhill, both of England

[73] Assignee: Beecham Group p.l.c., England

[21] Appl. No.: 479,953

[22] Filed: Mar. 29, 1983

[30] Foreign Application Priority Data

Mar. 31, 1982 [GB] United Kingdom ............ 8209426

[51] Int. Cl.³ .............. A61K 31/43; A61K 31/545; C07D 499/54; C07D 501/22
[52] U.S. Cl. .................... 514/193; 260/239.1; 514/194; 514/195; 514/196; 514/201; 514/203; 514/204; 514/206; 514/207; 514/202; 544/21; 544/22; 544/24; 544/25; 544/26; 544/27; 544/28; 544/29; 544/30; 544/90; 546/183
[58] Field of Search ............ 260/239.1; 544/21, 22, 544/28, 29, 27, 24, 25, 26, 30, 90; 424/246, 248.51, 248.52, 248.53, 271, 248.55, 248.57, 256; 546/183

[56] References Cited

U.S. PATENT DOCUMENTS 3,939,150 2/1976 Murakami et al. .......... 260/239.1
4,223,037 9/1980 Preiss et al. ............... 424/271
4,235,774 11/1980 Preiss et al. ............... 260/239.1

FOREIGN PATENT DOCUMENTS 0023045 1/1981 European Pat. Off.
1507623 4/1978 United Kingdom.

Primary Examiner—Natalie Trousof
Assistant Examiner—Vera C. Clarke
Attorney, Agent, or Firm—Jacobs & Jacobs

[57] ABSTRACT

A compound of formula (1) or a pharmaceutically acceptable salt or in vivo hydrolysable ester thereof:

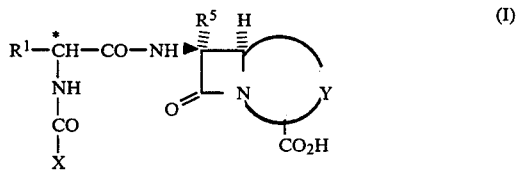

wherein
$R^1$ is phenyl, substituted phenyl or a 5- or 6-membered heterocyclic ring containing up to three heteroatoms selected from oxygen, sulphur or nitrogen, optionally substituted with hydroxy, amino, halogen or $C_{1-6}$ alkoxy;
X represents;

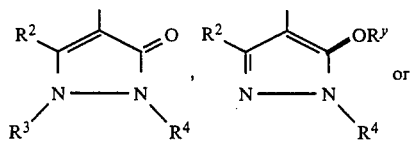

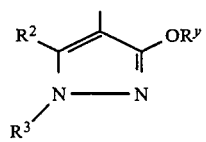

wherein $R^y$ is methyl or acetyl; $R^2$ and $R^3$ may be the same or different and each is hydrogen, an aryl group, a heterocyclyl group or a $C_{1-6}$ alkyl group optionally substituted by an aryl group or a heterocyclyl group; and $R^4$ is hydrogen, a $C_{1-6}$ alkylcarbonyl group, an aryl group, a heterocyclyl group, a $C_{1-6}$ alkyl group optionally substituted by an aryl group or a heterocyclyl group;
$R^5$ represents, hydrogen, methoxy or —NHCHO; and Y is:

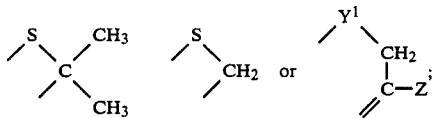

wherein $Y^1$ is oxygen, sulphur or —CH$_2$— and Z represents hydrogen, halogen or an organic group such as $C_{1-4}$ alkoxy, —CH$_2$Q or —CH=CH—Q wherein Q represents hydrogen, halogen, hydroxy, mercepto, cyano, carboxy, carbamoyloxy carboxylic ester, $C_{1-4}$ alkyloxy, acyloxy, aryl, a heterocyclyl group bonded via carbon, a heterocyclylthio group or a nitrogen containing heterocyclic group bonded via nitrogen.

24 Claims, No Drawings

β-LACTAM ANTIBACTERIAL AGENTS AND COMPOSITIONS CONTAINING THEM

This invention relates to a class of β-lactam derivative which have antibacterial activity and are of value in the treatment of infections in animals, including mammals and especially humans. In particular the invention relates to a class of β-lactam derivative with the pyrazolinone group in the acylamino side-chain. The invention also relates to a process for the preparation of such compounds, and to pharmaceutical compositions comprising them.

The present invention provides a compound of formula (1) or a pharmaceutically acceptable salt or in vivo hydrolysable ester thereof:

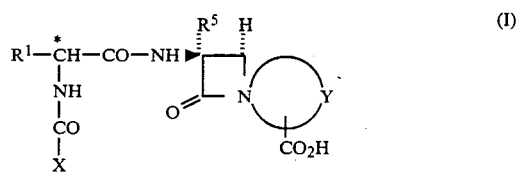

wherein $R_1$ is phenyl, substituted phenyl or a 5- or 6-membered heterocyclic ring containing up to three heteroatoms selected from oxygen, sulphur or nitrogen, optionally substituted with hydroxy, amino, halogen or $C_{1-6}$ alkoxy;

X represents;

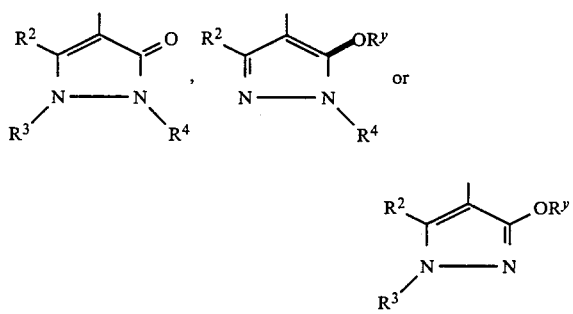

wherein $R^y$ is methyl or acetyl; $R^2$ and $R^3$ may be the same or different and each is hydrogen, an aryl group, a heterocyclyl group or a $C_{1-6}$ alkyl group optionally substituted by an aryl group or a heterocyclyl group; and $R^4$ is hydrogen, a $C_{1-6}$ alkylcarbonyl group, an aryl group, a heterocyclyl group, a $C_{1-6}$ alkyl group optionally substituted by an aryl group or a heterocyclyl group;

$R^5$ represents, hydrogen, methoxy or -NHCHO; and Y is:

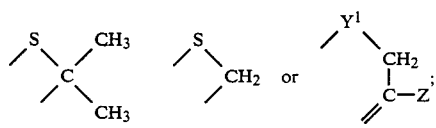

wherein $Y^1$ is oxygen, sulphur or —$CH_2$— and Z represents hydrogen, halogen or an organic group such as $C_{1-4}$ alkoxy, —$CH_2Q$ or —CH=CH—Q wherein Q represents hydrogen, halogen, hydroxy, mercepto, cyano, carboxy, carbamoyloxy carboxylic ester, $C_{1-4}$ alkyloxy, acyloxy, aryl, a heterocyclyl group bonded via carbon, a heterocyclylthio group or a nitrogen containing heterocyclic group bonded via nitrogen.

Suitably Y is —S—C(CH$_3$)$_2$—, —S—CH$_2$—, —S—CH$_2$—C(CH$_2$Q)=; or —O—CH$_2$—C(CH$_2$Q)=.

Preferred values for Y in the compounds of formula (I) are —S—C(CH$_3$)$_2$— and —S—CH$_2$C(CH$_2$Q)=, ie when the compound of formula (I) is a derivative of a penicillin and cephalosporin.

A particularly preferred value for Y is —S—C(CH$_3$)$_2$—.

Suitably $R^5$ is hydrogen
Suitably $R^5$ is methoxy
Suitably $R^5$ is —NHCHO
Suitably $R^2$, $R^3$ and $R^4$ are not all hydrogen atoms.
Suitably $R^2$, $R^3$ and $R^4$ are not all $C_{1-6}$ alkyl groups.
Preferably at least one of $R^2$, $R^3$ and $R^4$ is a hydrogen or $C_{1-6}$ alkyl group.
Preferably at least one of $R^2$, $R^3$ and $R^4$ is not a hydrogen atom or $C_{1-6}$ alkyl group.

Suitably the substituted phenyl group for $R^1$ is a phenyl group substituted with up to three groups selected from $C_{1-6}$ alkyl, phenyl, halogen, $C_{1-6}$ alkoxy, amino, nitro, hydroxy, $C_{1-6}$ alkylcarbonyloxy, carboxy, $C_{1-6}$ alkoxycarbonyl, halo ($C_{1-6}$) alkyl, oxo ($C_{1-6}$) alkyl, $C_{1-6}$ alkylcarbonyl, aryloxy, aralkyloxy, arylcarbonyl, $C_{1-6}$ alkylamino or di($C_{1-6}$) alkylamino.

Preferably $R^1$ is phenyl, 4-hydroxy phenyl, or 3,4-disubstituted phenyl wherein the substituents may be the same or different and are selected from chlorine, hydroxy, acetoxy and methoxy, or a 5- or 6-membered heterocyclic ring containing up to three heteroatoms selected from oxygen, sulphur or nitrogen, optionally substituted with hydroxy, amino, halogen or $C_{1-6}$ alkoxy.

Examples of suitable pharmaceutically acceptable in vivo hydrolysable ester groups include those which break down readily in the human body to leave the parent acid or its salts, for example acyloxyalkyl groups, such as acetoxymethyl, pivaloyloxymethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl groups, such as dimethylaminomethyl, dimethylaminoethyl, diethylaminomethyl or diethylaminoethyl; and lactone groups such as phthalidyl or dimethoxyphthalidyl.

Suitable pharmaceutically acceptable salts of the compounds of formula (I) include metal salts, eg aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylpiperidine, N-benzyl-β-phenethylamine, dehydroabietylamine, N,N'-bisdehydroabietylamine, ethylenediamine, or bases of the pyridine type such as pyridine, collidine or quinoline.

The carbon atom marked * in formula (I) is asymmetric and the compound may be derived from the side-chain having a D, L or DL configuration at that position. All forms of compound (I) are included in this invention. Suitably, the carbon atom marked * is derived from the D-configuration and is conveniently referred to as the D-penicillin.

Certain compounds within formula (I) may also occur in two or more tautomeric forms; these are also included within the scope of the present invention.

In formula (I), the group $R^1$ is preferably phenyl, 4-hydroxyphenyl, 3,4-dihydroxyphenyl, 2-thienyl, 3-thienyl or 2-amino-4-thiazolyl.

When used herein the term 'aryl' includes phenyl and naphthyl optionally substituted with up to three halogen, $C_{1-6}$ alkyl, $C_{1-6}$ alkoxy, halo ($C_{1-6}$) alkyl, hydroxy, amino, carboxy, $C_{1-6}$ alkoxycarbonyl, or $C_{1-6}$ alkoxycarbonyl-($C_{1-6}$)-alkyl, nitro, sulphonamido, $C_{1-6}$ alkylcarbonyl, amido(-CONH$_2$), $C_{1-6}$ alkylamino groups.

The term 'heterocyclyl' includes single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl, hydroxy, amino, carboxy, $C_{1-6}$ alkoxycarbonyl, $C_{1-6}$ alkoxycarbonyl(Cl-6) alkyl, aryl, oxo, nitro, sulphonamido, $C_{1-6}$ alkyl-carbonyl, amido or $C_{1-6}$ alkylamino groups.

When used herein the term 'halogen' unless otherwise defined is suitably fluorine, chlorine, bromine, and iodine, preferably chlorine and bromine.

When used herein the term 'carboxylic ester' unless otherwise defined suitably includes $C_{1-6}$ alkyl esters.

When used herein the term 'acyloxy' unless otherwise defined suitably includes $C_{1-6}$ alkylcarbonyloxy groups.

Suitable $C_{1-6}$ alkyl groups for $R^2$, $R^3$ and $R^4$ may be straight or branched chain and include methyl, ethyl n- or iso-propyl, n-, sec-, iso- or tert-butyl. In those cases where the $C_{1-6}$ alkyl group carries a substituent the preferred $C_{1-6}$ alkyl groups for $R^2$, $R^3$ and $R^4$ include methyl, ethyl and n-propyl.

Particular values of $R^2$ within the present invention include hydrogen, methyl and ethyl.

Particular values of $R^3$ within the present invention include methyl, ethyl and phenyl.

Particular values of $R^4$ within the present invention include hydrogen, methyl, ethyl and phenyl.

Since the β-lactam antibiotic compounds of the present invention are intended for use in pharmaceutical compositions it will readily be understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical it will readily be understood that the substantially pure form is preferred as for the β-lactam antibiotic compounds. Preferably, whenever possible, the compounds of the present invention are obtained in crystalline form.

Some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Suitable values for Q in the compounds of the formula (I) include the acetoxy, heterocyclylthio group, and nitrogen containing heterocyclic group bonded via nitrogen.

The heterocyclylthio group may suitably be represented by the formula:

—S—Het wherein 'Het' is a five or six membered heterocyclic ring containing from 1 to 4 atoms selected from N, O, and S unsubstituted or substituted with one or two groups selected from $C_{1-6}$ alkyl, $C_{1-6}$ alkoxy, hydroxyalkyl, $C_{1-6}$ alkenyl, alkoxyalkyl, carboxyalkyl, sulphonylalkyl, carbamoylalkyl, trifluoromethyl, hydroxy, halogen, oxo, (subst)aminoalkyl, and carboxyalkyl or two substituents may be linked to form the residue of a heterocyclic or carbocyclic ring.

Examples of the group 'Het' include unsubstituted and substituted imidazolyl, triazolyl, tetrazolyl, thiazolyl, thiadiazolyl, thiatriazolyl, oxazolyl, triazinyl and oxadiazolyl.

Suitable groups 'Het' include unsubstituted and substituted 1, 2, 3-triazolyl; 1, 2, 4-triazolyl; tetrazolyl; oxazolyl; thiazolyl; 1, 3, 4-oxadiazolyl; 1, 3, 4-thiadiazolyl, or 1, 2, 4-thiadiazolyl. Preferably the heterocyclylthio group is 1-methyl-1H-tetrazol-5-ylthio, 2-methyl-1,3,4-thiadiazol-5-ylthio, 1-carboxymethyl-1H-tetrazol-5-ylthio or 6-hydroxy-2-methyl-5-oxo-2H-1,2,4-triazin-3-ylthio.

The nitrogen containing heterocyclic group bonded via nitrogen is suitably an optionally substituted pyridinium group suitably the pyridinium group is substituted with one or two groups selected from $C_{1-6}$ alkyl, $C_{1-6}$ alkoxy, hydroxyalkyl, $C_{1-6}$ alkenyl, alkoxyalkyl, carboxyalkyl, sulphonylalkyl, carbamoylmethyl, carbamoyl, trifluoromethyl, hydroxy, halogen, oxo, and aminoalkyl.

One preferred subgroup within the present invention provides a compound of formula (II) or a pharmaceutically acceptable salt or in vivo hydrolysable ester thereof:

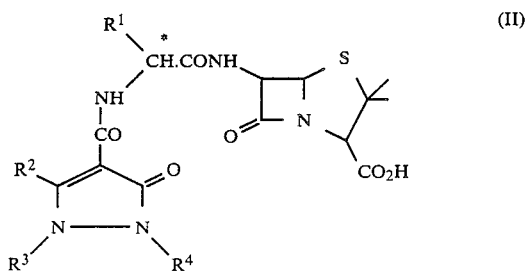

(II)

wherein $R^1$, $R^2$, $R^3$, $R^4$ and * are as hereinbefore defined.

Specific compounds within this invention include the following and pharmaceutically acceptable salts and in-vivo hydrolysable esters thereof:

(a) 6β- [D,2-(2,3-dimethyl-1-phenyl-3-pyrazolin-5-one-4-carbonylamino)-2-phenyl]acetamido penicillanic acid;

6β-[D,2-(2,3-dimethyl-1-phenyl-3-pyrazolin-5-one-4-carbonylamino)-2-(4-hydroxyphenyl)]acetamido penicillanic acid;

6β-[D,2-(2-phenyl-3-pyrazolin-5-one-4-carbonylamino)-2-phenyl] acetamido penicillanic acid; and (b) 6β-[D,2-(2H,3-Hydroxy-2-phenyl pyrazole-4-carbonyl amino)-2-phenyl] acetamido penicillanic acid;

6β-[D,2-(2H,3-Methoxy-2-phenylpyrazole-4-carbonylamino -2-phenyl] acetamido penicillanic acid;

6β-[D,2-(2-Ethyl-3-methyl-1-(4-nitrophenyl)-3-pyrazolin -5-one-4-carbonyl amino)-2-phenyl] acetamido penicillanic acid;

6β-[D2,-(2-Ethyl-3-methyl-1-(4-aminophenyl)-3-pyrazolin -5-one-4-carbonylamino)-2-phenyl-]acetamido penicillanic acid;

6β-[D,2-(2-Methyl-1-phenyl-3-pyrazolin-5-one-4-carbonyl amino)-2-phenyl] acetamido penicillanic acid;

6β-[D,2-(1-Benzyl-2-methyl-3-pyrazolin-5-one-4-carbonyl amino)-2-phenyl] acetamido penicillanic acid;

6β-[D,2-(2,3 Dimethyl-1-(4-bromophenyl)-3-pyrazolin-5-one-4-carbonyl amino)-2-phenyl] acetamido penicillanic acid;

6β-[D,2-(2-(4-Nitrophenyl)-3-pyrazolin-5-one-4-carbonyl amino)-2-phenyl] acetamido penicillanic acid;

6β-[D,2-(2-(4-Aminophenyl)-3-pyrazolin-5-one-4-carbonyl amino)-2-phenyl] acetamido penicillanic acid;

6β-[D,2-(2-(4-Nitrophenyl)-3-pyrazolin-5-one-4-carbonyl amino)-2-(4-hydroxy phenyl)] acetamido penicillanic acid;

6β-[D,2-(2-(4-Aminophenyl)-3-pyrazolin-5-one-4-carbonyl amino)-2-(4-hydroxy phenyl)] acetamido penicillanic acid;

6β-[D,2-(3-Methyl-2-phenyl-3-pyrazolin-5-one-4-carbonyl amino)-2-phenyl]acetamido penicillanic acid;

6β-[D,2-(4-Hydroxyphenyl-3-pyrazolin-5-one-4-carbonyl amino)-2-phenyl]acetamido penicillanic acid;

6β-[D,2-(2-p-Bromophenyl-3-pyrazolin-5-one-4-carbonyl amino)-2-phenyl]acetamido penicillanic acid;

7β-[D,2-(2-p-Nitrophenyl-3-pyrazolin-5-one-4-carbonyl amino)-2-phenyl]acetamido-3-acetoxymethyl-ceph-3-em-4-carboxylic acid;

7β-[D,2-(2-p-Aminophenyl-3-pyrazolin-5-one-4-carbonyl amino)-2-phenyl]acetamido-3-acetoxymethyl-ceph-3-em-4-carboxylic acid;

6β-[D,2-(2-[4-Methoxyphenyl]-pyrazol-3-in-5-one-4-carbonylamino)-2-phenyl]acetamido penicillanic acid;

6β-[D,2-([1H]-3-Methoxy-1-[4-nitrophenyl]pyrazole-4-carbonylamino)2-phenyl] acetamido penicillanic acid; and 6β-[D,2-([1H]-1-(4-Aminophenyl)-3-methoxy pyrazole-4-carbonylamino)-2-phenyl]acetamido penicillanic acid.

6β-[D,2-(2-[4-methylphenyl]pyrazol-3-in-5-one-4-carbonylamino)-2-phenyl]acetamido penicillanic acid; and 6β-[D,2 (2(p-4-hydroxy-n-butyl-1-amino)phenyl pyrazol-3-in-5-one-4-carbonylamino)-2-phenyl]acetamido penicillanic acid.

The compounds of formula (I) may be prepared by reacting a compound of formula (III):

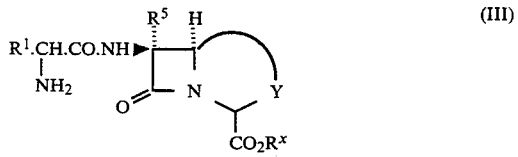

wherein the amino group is optionally substituted with a group which permits acylation to take place, $R^1$ is as defined with respect to formula (I) and any reactive substituents may be protected, and $R^x$ is hydrogen or a carboxyl-blocking group, with an N-acylating derivative of an acid $X—CO_2H$ wherein X is as hereinbefore defined and wherein any reactive groups may be protected; and thereafter, if necessary, carrying out one or more of the following steps:

(i) removing any carboxyl-blocking group $R^x$ (ii) removing any protecting groups on the side-chain group;

(iii) converting one group Z to a different group Z;

(iv) converting the product into a salt or in vivo hydrolysable ester thereof.

Suitable groups which permit acylation to take place and which are optionally present on the amino group of the starting material of the formula (II) include N-silyl, groups, for example trialkylsilyl groups such as trimethylsilyl; groups of formula $—P.R^aR^b$ wherein $R^a$ is an alkyl, haloalkyl, aryl, aralkyl, alkoxy, haloalkyl, aryl, aralkyl, alkoxy, haloalkoxy, aryloxy, aralkyloxy or dialkylamino group, $R^b$ is the same as $R_a$ or is halogen or $R^a$ and $R^b$ together form a ring; suitable such phosphorus groups being $—P(OC_2H_5)_2$, $—P(C_2H_5)_2$,

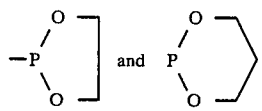

Suitable carboxyl-blocking derivatives for the group $—CO_2R^x$ in formula (III) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, allyl, p-toluenesulphonylethyl, methoxymethyl, a silyl or phosphorus-containing group, such as described above, an oxime radical of formula $—N=CHR^o$ where $R^o$ is aryl or heterocyclic, or an in vivo hydrolysable ester radical such as defined above.

The carboxyl group may be regenerated from any of the above esters by usual methods appropriate to the particular $R^x$ group, for example, acid—and base—catalysed hydrolysis, or by enzymically—catalysed hydrolysis, or by hydrogenation.

A reactive N-acylating derivative of the acid $X—CO_2H$ is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example, tertiary amine (such as triethylamine or dimethylaniline), an inorganic base (such as calcium carbonate or sodium bicarbonate) or an oxirane, which binds hydrogen halide liberatd in the acylation reaction. The oxirane is preferably a $(C_{1-6})$-1,2,alkylene oxide—such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as aqueous acetone, aqueous tetrahydroform, ethyl, acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid X—CO$_2$H or a salt thereof with a halogenating (eg chlorinating or brominating) agent such as phosphorus pentachloride, thionyl chloride or oxalyl chloride.

The acid chloride may also be prepared by reacting a compound of formula X—H, wherein X is as defined hereinbefore and wherein any reactive groups may be protected, with phosgene.

Alternatively, the N-acylating derivative of the acid X—CO$_2$H may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as p-toluenesulphonic acid). When a symmetrical anhydride is employed, the reaction may be carried out in the presence of 2,6-lutidine as catalyst.

Alternative N-acylating derivatives of acid X—CO$_2$H are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, or 8-hydroxyquinoline; or amides such as N-acylsaccharins or N-acylphthalimides; or an alkylidene iminoester prepared by reaction of the acid X—CO$_2$H with an oxime.

Other reactive N-acylating derivatives of the acid X—CO$_2$H include the reactive intermediates formed by reaction in situ with a condensing agent such as a carbodiimide, for example, N,N-diethyl-, dipropyl- or diisopropylcarbodiimide, N,N'-di-cyclohexylcarbodiimide, or N-ethyl-N'- -dimethylaminopropylcarbodiimide; a suitable carbonyl compound, for example, N,N'-carbonyldiimidazole or N,N'-carbonylditriazole; an isoxasolinium salt, for example, N-ethyl-5-phenylisoxazolinium-3-sulphonate or N-t-butyl-5-methylisozazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example BBr$_3$—C$_6$H$_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

The acid X—CO$_2$H and N-acylacylating derivatives thereof are novel compounds and form a further aspect of the present invention.

For the avoidance of doubt the acid X—CO$_2$H means the acids:

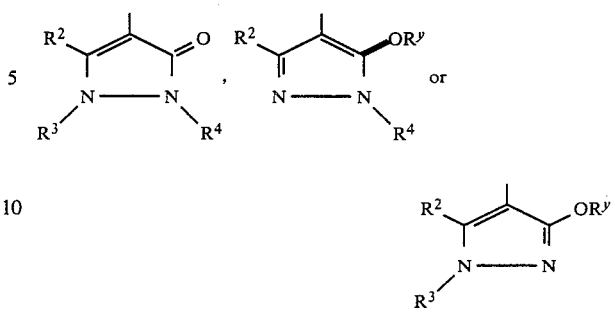

wherein R$^y$, R$^2$, R$^3$ and R$^4$ are as hereinbefore defined.

The intermediate compound of formula (III) may be prepared by reacting a compound of formula (IV):

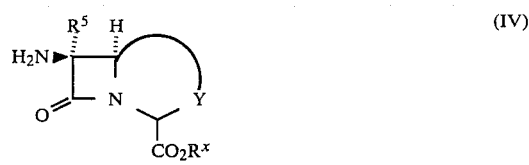

wherein the amino group is optionally substituted with a group which permits acylation to take place and R$^x$ and Y are as defined with respect to formula (I) above, with an N-acylating derivative of an acid of formula (V):

wherein R$^1$ is as defined with respect to formula (I) and any reactive groups therein may be protected and R$^y$ is an amino-protecting group; and thereafter removing protecting group R$^y$.

Suitable N-acylating derivatives, carboxyl protecting groups and reaction conditions include those described hereinbefore.

Suitable amino-protecting groups R$^y$ are those well known in the art which may be removed under conventional conditions without disruption of the remainder of the molecule.

The compounds of formula (I) may also be prepared by reacting a compound of formula (IV) as described hereinbefore with an N-acylating derivative of an acid of formula (VI):

wherein R$^1$ and X are as defined with respect to formula (I) and any reactive groups therein may be protected; and thereafter, if necessary, carrying out one or more of the following steps:

(i) removing any carboxyl-blocking group R$^x$;

(ii) removing any protecting groups on the side-chain group;

(iii) converting one group Z to a different qroup Z (iv) converting the product into a salt or in vivo hydrolysable ester.

The acid (VI) and N-acylating derivatives thereof are novel compounds and form a further aspect of the present invention.

The acid (VI) may be prepared by reacting an amino-acid of formula (VII):

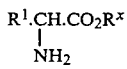

$$R^1.CH.CO_2R^x \atop NH_2 \qquad (VII)$$

wherein the amino group is optionally substituted with a group which permits acylation to take place, $R^1$ and $R^x$ are as defined hereinbefore with an N-acylating derivative of an acid $X$—$CO_2H$, wherein $X$ is as hereinbefore defined.

The present invention further provides a process for the preparation of a compound of formula (I) wherein $R^5$ is —NHCHO which process comprises formylating a compound of formula (VIII):

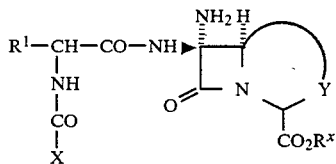

(VIII)

where any reactive groups may be protected; and thereafter, if necessary, carrying out one or more of the following steps:

(i) removing any carboxyl-blocking group $R^x$;
(ii) removing any protecting groups on the side chain group;
(iii) converting one group Z to a different group Z;
(iv) converting the product into a salt or in vivo hydroyable ester thereof.

Suitable formylating agents include mixed anhydrides such as formic acetic anhydride. The reaction may suitably be carried out in a temperature in the range −50° C. to 30° C. in aprotic solvent such as, for example, dichloromethane, chloroform, dimethylformamide, tetrahydrofuran, hexamethylphosphoramide, or dimethylsulphoxide, in the presence of a tertiary base. A preferred tertiary base employed in the reaction is a base of the pyridine type, such as pyridine, lutidine or picoline.

Compounds of the formula VIII may be prepared by the reaction of a corresponding compound of the formula (IX):

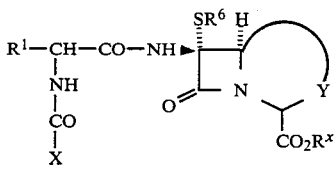

(IX)

wherein $Y, X, R^1 R^x$ are as hereinbefore defined, and $R^6$ is $C_{1-6}$ alkyl, aryl or benzyl; with anhydrous ammonia, an ammonium salt or an amine of the formula (X):

$$R^7—NH_2 \qquad (X)$$

wherein $R^7$ is a removable protecting group such as benzyl; in the presence of a metal ion such as mercury, silver, thallium, lead or copper and thereafter if necessary removing any protecting group to form the compound of formula (IX).

Suitable examples of the alkyl group for $R^6$ include $C_{1-6}$ alkyl groups such as methyl, ethyl, n-, or iso-propyl, and n-, sec-; iso-, or tert-butyl groups.

A preferred alkyl group for $R^6$ is methyl.

Suitable examples of the aryl group $R^6$ include phenyl, optionally substituted with $C_{1-6}$ alkyl, $C_{1-6}$ alkoxy, halogen, or nitro. Preferred aryl groups for $R^{19}$ include phenyl, o- m- or p-methylphenyl, o-, m- or p-nitrophenyl, in particular p-methylphenyl.

Suitable solvents in which the reaction may be performed include for example, diethylether, tetrahydrofuran, dimethylformamide, methanol and hexamethylphosphoramide. The reactions are generally carried out under an inert atmosphere and at moderate to low temperatures ie in the range −100° C. to 30° C. The course of the reaction may be followed by conventional methods such as thin layer chromatography and terminated when an optimum quantity of product is present in the reaction mixture.

The preferred metal ion for use in the above process is the mercuric ion, aptly in the form of mercuric acetate.

The intermediate compound of formula (IX) may suitably be converted to a compound of formula (I) wherein $R^5$ is methoxy by reaction with methanol in the presence of a metal ion such as mercury, silver, aluminium, lead or copper under conditions analogous to those described hereinbefore for the preparation of a compound of formula (VIII). It will be appreciated that the processes for preparation of a compound of formula (VIII) and (I) wherein $R^5$ methoxy described hereinbefore proceed via an imine intermediate; other processes proceeding via such an intermediate are also included herein.

The intermediate compound of formula (IX) is suitably prepared by acylation of the compound of formula (XI):

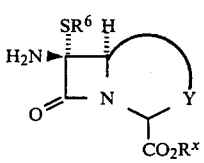

(XI)

with an acid of formula VI using methods analogous to those hereinbefore difined.

The sub-group of compounds within the present invention of formula (XIII):

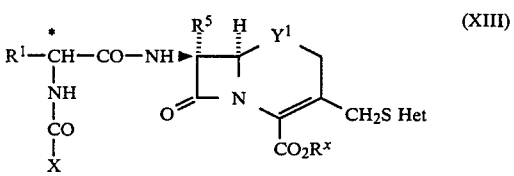

(XIII)

wherein $Y^1$, 'Het' $R^1$ and $R^5$ as defined hereinbefore may suitably be prepared by reacting a compound of formula (XIV):

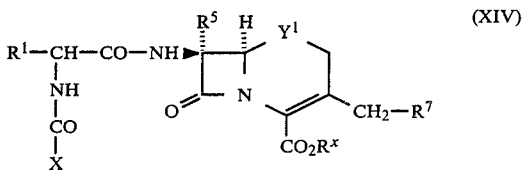

wherein $Y^1$, X, $R^1$ $R^5$ and $R^x$ are as defined hereinbefore and wherein any reactive groups may be protected and $R^7$ is a leaving group; with a thiol of formula:

HetSH with the proviso that when $R^7$ is an acyloxy group —$CO_2R^x$ must be in the free acid form or a salt thereof.

Suitable leaving groups $R^7$ include halogen such as iodide or bromide or an acyloxy groups such as, for example the acetyloxy group.

The thiol HetSH may be reacted as the free compound or a salt with an alkali metal such as sodium or potassium. This reaction is desirably conducted in a solvent. For example, use can be made of water, or organic solvents inert to the starting compounds, such as dimethylformamide, dimethylacetamide, dioxane, acetone, alcohol, 1,2-dichloroethane, acetonitrile, dimethylsulfoxide or tetrahydrofuran, or mixtures thereof. The reaction temperature and time depend, among other factors, upon the starting compounds and solvent to be employed but generally the reaction is carried out at a selected temperature within the range of 0° to 100° C. for a selected time of a few hours to several days. The reaction is desirably conducted between pH 3 and 7.

To prevent oxidation of the thio compounds it is advantageous to carry out the reaction in an inert gaseous atmosphere, eg nitrogen gas.

The subgroup of compounds within the present invention of formula (XV):

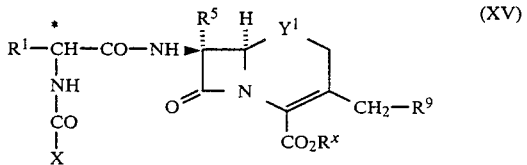

wherein $R^1$, $R^2$, $R^5$, and $Y^1$ are as defined hereinbefore and $R^9$ is an optionally substituted pyridinum group may suitably be prepared by reacting a compound of formula (XIV) as hereinbefore defined with the appropriately substituted pyridine.

Suitably the reaction with the pyridine is carried out in a polar solvent such as water, and in the presence of a catalyst such as an alkali metal thiocyanate or an alkali metal halide such as, for example sodium iodide.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The composition may be formulated for administration by any route, such as oral topical or parenteral. The compositions may be in the form of tablets, capsules, powders, granules, lozenges, creams or liquid preparations, such as oral or sterile parenteral solutions or suspensions.

Tablets and capsules for administration may be in unit dose presentation form, and may contain conventional excipients such as binding agents, for example syrup, acacia, gelatin, sorbitol, tragacanth, or polyvinylpyrolidone: fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flouring or colouring agents.

Suppositories well contain conventional suppository bases, e.g. coca-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parental suspensions are prepared in substanially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the composition comprise dosage units, each unit will preferably contain from 50–500 mg of the active ingredient. The dosage as employed for adult human treatment will preferably range from 100 to 3000 mg per day, for instance 1500 mg per day depending on the route and frequency of administration.

The compound of formula (I) may be the sole therapeutic agent in the compositions of the invention or a combination with other antibiotics or with a β-lactamase inhibitor may be employed.

Advantageously, the compositions also comprise a β-lactamase inhibitor of formula (XVI) or a pharmaceutically acceptable salt or ester thereof:

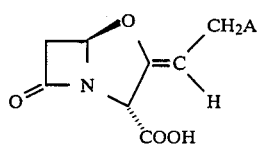

wherein A is hydroxyl, substituted hydroxyl, thiol, substituted thiol, amino, mono- or di-hydrocarbyl-substituted amino, or mono- or di-acylamino.

A further advantageous composition comprises a compound of formula (I) or a pharmaceutically acceptable salt or in vivo hydrolysable ester thereof together with a β-lactamase inhibitor of formula (XVII) or a pharmaceutically acceptable salt or in vivo hydrolysable ester thereof:

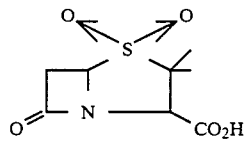

Further suitable β-lactamase inhibitors include 6B-bromopenicillanic acid and salts and in vivo hydrolysable esters and β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention.

The antibiotic compounds of the present invention are active against a broad range of gram positive and gram negative bacteria, in particular they are useful for treatment of respiratory tract and urinary tract infections in humans and mastitis in cattle.

The antibiotic compounds of the present invention are active against a wide range of gram negative and gram positive organisms including *E.coli* such as, for example ESS, JT4, JT425 and NCTC 10418; Pseudomonas Spp. such as *Ps. aeruginosa* for example 100662 and Dalgleish; *Serratia marcescens* US32; *Klebsiella aerogenes A*; *Enterobacter cloacae Nl*; *P.mirabilis* such as, for example C977 and 889; *P.morganii*; *P.rettgeri*; *B.subtilis*; *Staph aureus* such as, for example Oxford and Russell; *N.catarrhalis* 1502; *Strep faecalis I*; B-Haemolytic Strep CN10. The MIC data incl uded in the following examples is representative of the activity of the com pounds of the present invention.

The following Examples illustrate the preparation and use of the compounds of the present invention.

EXAMPLE 1

6β-[D,2-(2,3-dimethyl-1-phenyl-3-pyrazolin-5-one-4-carbonylamino)-2-phenyl]acetamido penicillanic acid, sodium salt 2,3-Dimethyl-1-phenyl-3-pyrazolin-5-one-4-carboxylic acid (0.186 g, 0.8 mmol) in dry dimethyl formamide (D.M.F) (4 ml) was treated with triethylamine (0.12 ml, 0.8 mmol). The solution was cooled to −10° C. and isobutyl chloroformate (0.10 ml, 0.76 mmol) added dropwise. After 1 hour at −10° C., solids were removed by filtration and the solution added to ampicillin (anhydrous) (0.28 g, 0.8 mmol) premixed with triethylamine (0.12 ml, 0.8 mmol) in D.M.F. (10 ml) at −40° C. The solution was allowed to warm to 0° C., stirred for 90 minutes and poured into excess dry ether, with stirring. The precipitate was isolated and partitioned between ethyl acetate and water. The pH was adjusted to 7.5 (bicarbonate addition); the aqueous layer separated and acidified to pH 1.5 (HCl(5N)). Extraction with ethyl acetate, drying ($Na_2SO_4$) and evaporation gave the title product as the free penicillanic acid (0.09 g, 20%), δ(($CD_3$)$_2$CO) 1.50, 1.58 (2×3H, 2s, ($CH_3$)$_2$), 2.68 (3H, s, =C—$CH_3$), 3.34 (3H, s, —N$CH_3$), 4.36 (1H, s, $C_3$-proton), 5.53 (1H, d, J 4 Hz, $C_5$-proton), 5.71 (1H, d of d, J 4, 8 Hz, $C_6$-proton), 5.94 (1H, d, J 8 Hz, —CHCON—), 7.53 (10H, complex, aryl protons), 8.20 (1H, d, J 8 Hz, —NH—), 9.78 (1H, d, J 8 Hz, —NH—), 6.5–9 (1H, br, —$CO_2$H). The free acid was converted to the sodium salt by addition, to an acetone solution of the free acid, of a solution of sodium ethylhexanoate (0.084 ml, 1.9N) in methyl isobutyl ketone, further addition of ether, and filtration of the precipitate. The sodium salt (2) showed $v_{max}$ (nujol) 1780, 1760, 1690, 1655, 1600 cm$^{-1}$.

MIC against *E. coli* NCTC 10418 5.0 μglml.

EXAMPLE 2

6β-[D,2-(2,3-dimethyl-1-phenyl-3-pyrazolin-5-one-4-carbonylamino)-2-(4-hydroxyphenyl)]acetamido penicillanic acid, sodium salt The free penicillanic acid of the title compound was prepared in the same manner as in Example 1, except that amoxycillin trihydrate was used in place of ampicillin. The free acid possessed δ (deuterio-acetone +$D_2O$) 1.52, 1.62 (2×3H, 2s, ($CH_3$)$_2$), 2.68 (3H, s, =C—$CH_3$), 3.34 (3H, s, —N—$CH_3$), 4.40 (1H, s, $C_3$-proton), 5.54 (1H, d, J4 Hz, $C_5$-proton), 5.72 (1H, d, J4 Hz, $C_6$-proton), 5.82 (1H, s, CHCO.N), 6.85 (2H, d, J 8 Hz, aryl protons o- to OH), 7.44 (7H, complex, other aryl protons). In the absence of $D_2O$ there are also present 8.69 (1H, d, J 7 Hz, —NH—), 9.69 (1H, d, J 7 Hz, —NH—).

The free acid was converted to the sodium salt (obtained in 36% overall yield) by suspension in water, addition of dilute sodium bicarbonate solution until, on shaking, dissolution occurred at pH 5.5, and freeze-drying. The sodium salt (3) possessed $v_{max}$ (nujol) 1780–1760, 1680, 1640, 1610 cm$^{-1}$. MIC against *E. Coli* NCTC10418 12.5 μg/ml.

EXAMPLE 3

6β-[D,2-(2-phenyl-3-pyrazolin-5-one-4-carbonylamino)-2-phenyl]acetamido penicillanic acid, sodium salt (a) 4-Ethoxycarbonyl-2-phenyl-3-pyrazolin-5-one This preparation is based on that of Cheng and Robins, *J. Org. Chem.*, 1956, 21, 1240.

Ethoxymethylene malonate (2.16 ml, 10.0 mmol) was added to N'-acetyl-N-phenylhydrazine (1.8 g, 12.0 mmol) in phosphorus oxychloride (30 ml) and the mixture stirred at 90° C. for 5 hours.

On pouring into water, a yellow precipitate formed. The aqueous solution was further extracted with ether which was dried and evaporated to give, on combination with the filtered precipitate, a total yield of the title compound of 0.83 g (38%). Recrystallisation from aqueous ethanol gave mp 123°, $\nu_{max}$ (CHCl$_3$) 1710, 1680, 1600, 1585 cm$^{-1}$, δ (CDCl$_3$) 1.38 (3H, t, J 8 Hz, —OCCH$_3$), 4.35 (2H, q, J 8 Hz, —OCH$_2$—), 7.45 (5H, m, aryl protons), 8.05 (1H, s, pyrazoline-3-proton).

(b) 2 Phenyl-3-pyrazolin-5-one-4-carboxylic acid

4-Ethoxycarbonyl-2-phenyl-3-pyrazolin-5-one (0.24 g, 1 mmol) was heated in 1N NaOH solution (10 ml) at reflux for 3 hours. Cooling and acidification (5N HCl) gave the title compound as a precipitate (0.20 g, 96%), mp 196°–8° C., $\nu_{max}$ (nujol) 3200–2500 (br) 1710, 1680, 1585, 1515 cm$^{-1}$, δ ((CD$_3$)$_2$CO+D$_2$O) 7.40 (5H, complex, aryl protons), 8.58 (1H, s, pyrazoline-3-proton).

(c) 6β-[D,2-(2-phenyl-3-pyrazolin-5-one-4 carbonyl amino)-2-phenyl]acetamido penicillanic acid The title compound was prepared from 2-phenyl-3-pyrazolin-5-one-4-carboxylic acid obtained in (b) above in a manner analogous to Example 1. The free acid possessed δ ((CD$_3$)$_2$CO+D$_2$O) 1.50, 1.58 (2×3H, 2s, (CH$_3$)$_2$), 4.32 (1H, s, C$_3$-proton), 5.48 (1H, d, J 4 Hz, C$_5$-proton), 5.64 (1H, d, J 4Hz, C$_6$-proton), 5.92 (1H, s, —CHCON—), 7.55 (11H, complex, aryl and 3-pyrazoline protons), 8.55 (1H, s, —CONH—). Prior to D$_2$O addition also observed was 7.70 (1H, brd, J8 Hz, CONH—). The sodium salt possessed $\nu_{max}$(nujol) 1760, 1670, 1640, 1600 cm$^{-1}$. M.I.C. against E. coli NCTC 10418, 2.5 μg/ml.

EXAMPLE 4  6μ-[D,2-(2H,3-Hydroxy-2-phenyl pyrazole-4-carbonyl amino)-2-phenyl]acetamido penicillanic acid (sodium salt)

(a) 2H,3-Hydroxy-2-phenyl pyrazole-4-carboxylic acid 2H,4-Ethoxycarbonyl-3-hydroxy-2-phenyl pyrazole (2.275 g, 9.8 mmol) in 7.5% sodium hydroxide solution (30 ml) was stirred at 80° C. under nitrogen for 3½ hours. The reaction mixture was allowed to cool and washed twice with ethyl acetate. The aqueous solution was then acidified (5N HCl) to pH 1.5 whereupon the desired acid precipitated out and was filtered and washed with water, followed by drying in Vacuum. (2.1 g, 98%)

$\nu$max (Nujol) 1690,1620,1599,1560,1500 cm$^{-1}$ δ(D$_6$-DMSO) 7.65(7H,m,phenyl protons, C$_5$ pyrazole proton, hydroxy proton (exchangeable D$_2$O)), 9.89 (1H, bs, acid OH (exchangeable D$_2$O)). Found: M$^+$, 204.0526; C$_{10}$H$_8$N$_2$O$_3$ requires M,204.0535

(b) 6β-[D,2-(2H,3-Hydroxy-2-phenyl pyrazole-4-carbonyl amino)-2-phenyl]acetamido penicillanic acid (sodium salt)

The acid prepared as in (a) above (359 mg, 1.75 mmol) in dry dichloromethane (10 ml) was treated at room temperature with triethylamine (265 μl, 1.76 mmol) and then cooled to −20° C. and treated with thionyl chloride (132 μl, 1.75 mmol) in dichloromethane (4 ml). The whole was then stirred for 1 hour at −20° C.

Simultaneously Ampicillin (611 mg, 1.75 mmol) in dry dichloromethane (10ml) was treated with triethylamine (495 μl, 3.52mmol) and the mixture stirred for 30 mins to give a solution of the triethylamine salt. The ampicillin solution was cooled to −20° C. and treated with the acid chloride from above. The whole was then allowed to warm to room temperature and stirred for 2 hours. The dichloromethane was then evaporated and the residue partitioned between ethyl acetate and dilute sodium bicarbonate solution at pH 7.5. Subsequent separation and acidification (HCl) to pH 1.5 of the aqueous layer produced a precipitate of the desired penicillin free acid which was filtered and washed with water. The free acid was converted to the disodium salt by suspension in water, addition of dilute sodium bicarbonate solution until, on shaking, a dissolution occurred at pH 6.8, and freeze-drying (204 mg)

$\nu$ max (Nujol) (sodium salt) 1760,1720,1590,1215 cm$^{-1}$; δ (free acid) (D$_6$Acetone+D$_2$O) 1.50,1.60 (6H,2s, gem dimethyls), 4.38 (1H,s,C3-penicillin proton), 5.60 (3H,M, C$_5$, C$_6$ protons and —CH —CONH—), 7.55 (11H,m, ampicillin phenyl protons, C$_5$ pyrazole proton, pyrazole phenyl protons).

MIC against E. Coli NCTC 10418 2 μg/ml.

EXAMPLE 5

6β-[D,2-(2H,3-Methoxy-2-phenylpyrazole-4-carbonylamino-2-phenyl]acetamido penicillanic acid, sodium salt (a) 2H, 4-Ethoxycarbonyl-3-methoxy-2-phenylpyrazole 2H,4-Ethoxycarbonyl-3-hydroxy-2-phenyl pyrazole (1 mmol, 232 mg) in dry dimethylformamide (10 ml) with potassium carbonate (1 mmol, 138 mg) was treated with methyl iodide (2 mmol, 124 μl) and the whole was then stirred under nitrogen at 40° C. overnight.

The reaction mixture was added dropwise to ether (300 ml) and the ether washed with water (4×100 ml). The ether solution was subsequently dried (MgSO$_4$) and evaporated to yield the title product as a white solid (163 mg,69%) which was recrystallised from aqueous ethanol, mp 67°, $\nu$max (CHCl$_3$) 1710, 1599, 1565, 1505cm$^{-1}$ δ(CDCl$_3$) 1.38 (3H, t, J6.5 Hz,—OCH$_2$CH$_3$), 4.17 (3H,s,—OMe), 4,34 (2H,q, J6.5 Hz,—OCH$_2$CH$_3$), 7.6 (5H,m,phenyl protons), 8.02 (1H,s,-C$_5$ pyrazole proton).

Found: M$^+$, 246.1012; C$_{13}$H$_{14}$N$_2$O$_3$ requires M,246.1004.

(b) 2H, 3-Methoxy-2-phenyl pyrazole-4-carboxylic acid

The ester prepared as described in (a) above (390 mg, 1.58 mmol) in 1N sodium hydroxide (10 ml) was refluxed for 3 hours under nitrogen and then allowed to cool and the solution was washed with ethyl acetate. The aqueous layer was then acidified to pH 2(HCl) whereupon the title compound precipitated out and was filtered and washed with water followed by drying under vacuum (268 mg, 78%), $\nu$max (Nujol) 1680, 1595, 1560 cm$^{-1}$ δ (D$_6$-Acetone) 4.24 (3H,s,—OCH$_3$),7.74 (5H,m, phenyl protons), 8.06 (1H,s,C$_5$ pyrazole proton), Found M$^+$; 218.0684, C$_{11}$H$_{10}$N$_2$O$_3$ Requires M,218.0689.

(c) 6β-[D,2-(2H,3-Methoxy-2-phenyl-pyrazole-4-carbonylamino)-2-phenyl]acetamido penicillanic acid, sodium salt The acid prepared in (b) above (218 mg, 1 mmol) in dry dichloromethane (5 ml) was treated with triethylamine (1 mmol, 140 μl ) to give a solution which was cooled to −10° C. and treated with thionyl chloride (1 mmol, 75 μl) in dry dichloromethane (2 ml). The whole was then stirred at −10° for 1 hour.

Simultaneously Ampicillin (1 mmol, 349 mg) in dry dichloromethane (5 ml) was treated with triethylamine (2 mmol 1,280 μl) and the mixture stirred for 20 mins to give a solution of the triethylamine salt. The ampicillin solution was cooled to −15° C. and treated with the acid chloride from above. The whole was allowed to warm to 0° C. and stirred for 90 mins. At the end of this time the dichloromethane was evaporated and the residue partioned between ethyl acetate and dilute sodium bicarbonate solution at pH 7.5. The aqueous layer was subsequently separated and acidified (HCl) to pH 1.5. Ethyl acetate extraction of this produced, on drying (MgSO$_4$) and evaporaton, the desired penicillin free acid (293 mg). The free acid was converted to the monosodium salt by suspension in water, addition of dilute sodium bicarbonate until on shaking at pH 5.5 dissolution occurred, and freeze-drying.

$\nu$max (nujol) (sodium salt) 1765cm$^{-1}$, $\delta$(free acid) (D$_6$Acetone +D$_2$O) 1.45, 1.53 (6H, 2s, gem dimethyls), 3.96 (3H, s, —OMe), 4.32 (1H, s, C$_3$ penicillin proton), 5.57 (2H, ABq, J4 Hz C$_5$ and C$_6$ penicillin protons), 5.95 (1H, s, —CH—CO.N—), 7.6 (11H, m, C$_5$ pyrazole proton, pyrazole phenyl protons, penicillin phenyl protons).

MIC against *E.Coli* NCTC 10418 12.5 $\mu$g/ml.

EXAMPLE 6

6$\beta$-[D,2-(2-Ethyl-3-methyl-1-(4-nitrophenyl)-3-pyrazolin-5-one-4-carbonyl amino)-2-phenyl]acetamido penicillanic acid (a)
2-Ethyl-3-methyl-1-(4-nitrophenyl)-3-pyrazolin-5-one-4-carboxylic acid 2-Ethyl-3-methyl-1-(4-nitrophenyl)-3-pyrazolin-5-one (2.47 g, 10 mmol) in dry chloroform (10 ml) was treated with 12.5% phosgene in toluene (16 ml) and the whole stirred at 50° C. for 1 hour. The reaction solution was then concentrated by evaporation, 1N sodium hydroxide (30 ml) added and the mixture stirred for 10 minutes. The aqueous layer was then separated and acidified (HCl) to pH 1.5 followed by ethyl acetate extraction. Drying and evaporation of the ethyl acetate layer produced 330 mg of crude material consisting of a 1:1 mixture of starting pyrazolinone and desired acid.

The desired acid was separated by partioning the crude product between dilute sodium bicarbonate solution and ethyl acetate, followed by separation and acidification (HCl) to pH 1.5 of the aqueous layer, from which the desired acid was obtained by ethyl acetate extraction (151 mg). $\nu$max (Nujol) 1730, 1715, 1630, 1590cm$^{-1}$ $\delta$(D$_6$Acetone) 1.12 (3H,t,J7Hz-NCH$_2$CH$_3$), 2.80(3H,s,C$_3$Me),4.18 (2H,q,J7Hz-NCH$_2$CH$_3$), 6.55(1H, bs,acid-OH, exchangeable D$_2$O), 7.88 (2H,d,J9 Hz, protons m-NO$_2$), 8.59(2H,d,J9 Hz, protons o-NO$_2$), Found:M$^+$, 291.0854; C$_{13}$H$_{13}$N$_3$O$_5$ requires M, 291.0854.

(b) 6$\beta$-[D,2-(2-Ethyl-3-methyl-1-(4-nitrophenyl)-3-pyrazolin-5-one-4-carbonylamino)-2-phenyl]acetamido penicillanic acid The acid, prepared as described above in (a), (157 mg, 0.51 mmol) in dry dimethyl formamide (4 ml) was treated with triethylamine (80 $\mu$l,0.51 mmol). The resultant solution was cooled to −10° C. and treated dropwise with isobutylchloroformate (65 $\mu$l,0.5 mmol. The mixture was stirred at −10° C. for 1 hour and then cooled to −30° C. and the solids filtered off.

Simultaneously, Ampicillin (0.5 mmol,175 mg) in dry dimethyl formamide (5 ml) was treated with triethylamine (0.5 mmol, 80 $\mu$l) and stirred for 20 mins to give a solution of the triethylamine salt. The ampicillin solution was cooled to −40° C. and treated dropwise with the mixed anhydride from above. The whole was then allowed to warm to 0° C. and stirred for 2 hours.

The reaction mixture was added dropwise to 100 ml dry diethyl ether. The solids obtained were partioned between ethyl acetate and dilute sodium bicarbonate at pH 7.5. The aqueous layer was separated and acidified (HCl) to pH 1.5, subsequent ethyl acetate extraction of which gave on drying (MgSO$_4$) and evaporation, the desired penicillin free acid (34 mg). This was converted to the sodium salt by suspension in water, addition of dilute sodium bicarbonate solution until on shaking at pH 5.8 dissolution occurred, followed by freeze drying.

$\nu$ max(Nujol) (Sodium Salt). 1760cm$^{-1}$ $\delta$(free acid) (D$_6$Acetone) 1.0-(3H,t,J7Hz,-NCH$_2$CH$_3$), 1.55 (6H,2s, gem dimethyls), 2.75(3H,s, C3 methyl), 4.02(2H,q,J7Hz,-NCH$_2$CH$_3$), 4.33(1H,s,C3 penicillin proton), 5.75 (3H,m,C$_5$,C$_6$ protons and —CH CONH—), 6.10 (1H,bs,—OH proton, exchangeable D$_2$O), 7.50 (5H, m, ampicillin phenyl protons), 7.75(2H,d,J9Hz, protons, m-toNO$_2$), 8.46(2H,d,J9 Hz, protons oNO$_2$), 8.11(1H,d,J7Hz—NH), 9.88(1H,d,J8 Hz,—NH)

MIC against *E.Coli* NCTC 10418 25 $\mu$g/ml.

EXAMPLE 7

6$\beta$-[D2,-(2-Ethyl-3-methyl-1-(4-aminophenyl)-3-pyrazolin-5-one-4-carbonylamino)-2-phenyl]acetamido penicillanic acid (sodium salt)

The penicillin sodium salt prepared as described in example (6b) (89 mg, 0.13 mmol) in water (4 ml) was treated with 10% Palladium|Charcoal catalyst (80 mg) and the whole hydrogenated at S.T.P. for 3 hours.

The catalyst was then removed by filtration through celite and the celite washed thoroughly with water; freeze drying of the filtrate gave the desired penicillin sodium salt (49 mg)

$\nu$ max (Nujol)1770cm$^{-1}$ $\delta$ (D$_2$O)1.08(3H,m,-NCH2CH$_3$), 1.64 (6H,m, gem dimethyls), 2.73(3H,s,C$_3$—Me), 3.8 (2H,m,—NCH$_2$CH$_3$), 4.30(1H,s,C$_3$penicillin proton), 5.68(2H,m,C5,C6 protons), 5.87 (1H, bs,—CH—CONH—), 7.22(4H, bs, pyrazole phenyl protons), 7.63 (5H, bs, ampicillin phenyl protons)

MIC against *E. coli* NCTC 1048 50 $\mu$g/ml.

EXAMPLE 8

6$\beta$-[D,2-(2-Methyl-1-phenyl-3-pyrazolin-5-one-4-carbonyl amino)-2-phenyl] acetamido penicillanic acid, sodium salt (a) 1-phenyl-3-pyrazolin-5-one 4-Ethoxycarbonyl-1-phenyl-3-pyrazolin-5-one (2.139 g, 9.2 mmol) in 1N sodium hydroxide (50 ml) was stirred under nitrogen at vigorous reflux for three hours. The reaction mixture was allowed to cool and acidified (HCl) to pH 3.5, whereupon ethyl acetate extraction, followed by drying (MgSO$_4$) and evaporation produced the desired product (1.072 g, 72%) $\delta$ max(CHCl$_3$) 1705, 1595, 1495 cm$^{-1}$ $\delta$(D$_6$-DMSO) 5.60 (1H,d,J2 Hz, C$_4$ proton), 7.60 (6H, m, phenyl protons and C$_3$ proton) Found; M+; 160.0641. C$_9$H$_8$N$_2$O$_6$ requires M; 160.0637.

(b) 2-Methyl-1-phenyl-3-pyrazolin-5-one

The pyrazolinone prepared as described above in (a) (1.153 g, 7.2 mmol) in dry toluene (3 ml) was treated with dimethyl sulphate (8 mmol, 750 $\mu$l) and the whole refluxed under nitrogen for 5 hours. The reaction mixture was then allowed to cool and in doing so separated into two phases. The upper consisting mainly of toluene was carefully pipetted off and discarded. The remaining layer was then treated with water (1 ml), the whole warmed with stirring to 50° C. and then treated with 40% sodium hydroxide solution (1 ml) and stirred at 50° C. for a further 30 minutes. The resultant solution was subsequently extracted with three portions of benzene. The first two extracts were found to contain two products which has spectral properties consistent with 2-methyl-1-phenyl-3-pyrazolin-5-one and 2,4-dimethyl-1-phenyl-3-pyrazolin-5-one. These were separated by chromatography on silica (ethyl acetate) to give 2-methyl-1-phenyl-3-pyrazolin-5-one (95 mg). The third extracton (above) consisted solely of 2-methyl-1-phenyl-3-pyrazolin-5-one (208 mg) (Total yield, 24%). $\nu_{max}$ (CHCl$_3$) 1655, 1595, 1550, 1495 cm$^{-1}$. δ(D$_6$ Acetone) 3.11 (3H, s, —NMe), 5.44 (1H, d, J4 Hz, C4 proton), 7.47 (5H, m, phenyl protons), 7.83 (1H, d, J4 Hz, C$_3$ proton). Found: M+ 174.0798; C$_{10}$H$_{10}$N$_2$O requires M; 174.0794.

(c)
6β-[D,2-(2-Methyl-1-phenyl-3-pyrazolin-5-one-4-carbonylamino)-2-phenyl]acetamido penicillanic acid (sodium salt)

The pyrazolinone prepared as described in (b) above (248 mg, 1.42 mmol) in dry chloroform (10 ml) was treated with 12.5% phosgene in toluene (2.3 ml) and the whole stirred at 50° C. for 1.75 hr. The reaction mixture was then further treated with 12.5% phosgene in toluene (2.3 ml) and the whole stirred overnight at room temperature. The reaction solution was then evaporated to dryness and the residue redissolved in fresh, dry chloroform. The solution was then added dropwise to predissolved Ampicillin (500 mg, 1.42 mmol) in dry dichloromethane (10 ml) containing triethylamine (2.84 mmol, 426 μl), stirring at −30° C. The whole was then allowed to warm to room temperature and stirred for 2 hours. One drop of 5N hydrochloric acid was then added and the dichloromethane evaporated. The residue was then partitioned between ethyl acetate and dilute sodium bicarbonate solution at pH 7.5. Separation of the aqueous layer and subsequent acidification (HCl) to pH 1.5 followed by ethyl acetate extraction, drying (MgSO$_4$) and evaporation produced the crude pencillin (80 mg). This was purified by chromatography on silica (5:4:1 ethyl acetate:isopropanol:water). The free acid was then converted to the sodium salt (60 mg) by the method described in example 6(b). $\nu_{max}$ (Nujol) 1765 cm$^{-1}$. δ(Free acid). (CD$_3$OD) 1.46, 1.56 (2×3H, 2s, gemdimethyls), 3.50 (3H, s, —NMe), 4.31 (1H, s, C$_3$ penicillin proton), 5.48 (2H, m, C$_5$ and C$_6$ penicillin protons), 5.75 (1H, s, —CH—CONH—), 7.40 (10H, m, aromatic protons), 8.24 (1H, s, C$_3$ pyrazole proton), 8.88 (1H, d, J7 Hz —NH, slowly exchanges), 9.24 (1H, d, J7 Hz, —NH slowly exchanges).

MIC against *E.Coli* NCTC 10418 10 μg/ml.

EXAMPLE 9

6β-[D,2-(1-Benzyl-2-methyl-3-pyrazolin-5-one-4-carbonyl amino)-2-phenyl]acetamido penicillanic acid (sodium salt)

(a) 1-Benzyl-4-ethoxycarbonyl-3-pyrazolin-5-one

Benzyl hydrazine (324 mg, 2.65 mmol) in water (15 ml) containing potassium carbonate (368 mg, 2.65 mmol) was treated with diethyl ethoxymethylene malonate (575 μl, 2.65 mmol) and the whole refluxed for 3 hours. The reaction mixture was allowed to cool and then washed with ethyl acetate. The aqueous solution was then acidified (HCl) to pH 2 and extracted with ethyl acetate. The ethyl acetate extraction was dried (MgSO$_4$) and evaporated to give the title product as an oily solid which solidified on hexane trituration 265 mg, 41%), recrystallised from aqueous ethanol, mp 79°-81° C. $\nu_{max}$ (CHCl$_3$) 1720, 1659, 1575 cm$^{-1}$. δ(CDCl$_3$) 1.37 (3H, t, J8 Hz, —OCH$_2$CH$_3$), 4.4 (2H, q, J8 Hz, OCH$_2$CH$_3$), 5.23 (2H, s, —CH$_2$N), 7.44 (5H, m, phenyl protons), 7.73 (1H, s, C$_3$ pyrazole proton), 8.50 (1H, bs, —NH proton). Found: M+, 246.0995; C$_{13}$H$_{14}$N$_2$O$_3$ requires M, 246.1003.

(b)
1-Benzyl-4-ethoxycarbonyl-2-methyl-3-pyrazolin-5-one

The ester prepared as described above in (a) (1.172 g, 4.76 mmol) in 1N NaOH (5 ml) was treated with dimethyl sulphate (885 μl, 9.28 mmol) and the whole stirred at room temperature for 5 hours. Further excess sodium hydroxide solution was then added and the solution stirred for 20 minutes. The aqueous reaction mixture was then extracted with chloroform to give, after drying (MgSO$_4$) and evaporation, 809 mg of crude material which was found to consist of the desired 1-benzyl-4-ethoxycarbonyl-2-methyl-3-pyrazolin-5-oneand 1-benzyl-4-ethoxycarbonyl-5-methoxy pyrazole. The desired N-alkylated product was subsequently separated by chromatography on silica (EtOH:EtOAc). (587 mg). Recrystallisation from ethyl acetate gave mp 119°-121° C. $\nu_{max}$ (CHCl$_3$) 1725, 1660, 1565 cm$^{-1}$, δ(CDCl$_3$) 1.34 (3H, t, J7 Hz, —OCH$_2$CH$_3$), 3.50 (3H, s, —NMe), 4.30 (2H, q, J7 Hz, —OCH$_2$CH$_3$), 5.14 (2H, s, PhCH$_2$N), 7.26 (5H, s, phenyl protons), 7.82 (1H, s, C$_3$ pyrazole proton). Found: M+, 260.1165; C$_{14}$H$_{16}$N$_2$O$_3$ requires M, 260.1158.

(c) 1-Benzyl-2-methyl-3-pyrazolin-5-one-4-carboxylic acid

The ester prepared as described in (b) above (260 mg, 1 mmol) in 10% NaOH was stirred at an oil bath temperature of 90° C. for 1.5 hours. The reaction mixture was then allowed to cool and was washed with ethyl acetate. The aqueous solution was acidified (HCl) to pH 1.5 whereupon the desired acid precipitated out and was filtered and washed with water, followed by drying under vacuum (202 mg), $\nu_{max}$(Nujol) 1710, 1660 cm$^{-1}$ δ(D$_6$Acetone) 3.72 (3H, s, —NMe), 5.30 (2H, s, Ph—CH$_2$N), 7.33 (5H, s, phenyl protons), 8.20 (1H, s, C$_3$ pyrazole proton). Found: M+; 232.0858; C$_{12}$H$_{12}$N$_2$O$_3$ requires M, 232.0847.

(d)
6β-[D,2-(1-Benzyl-2-methyl-3-pyrazolin-5-one-4-carbonylamino)-2-phenyl]acetamido penicillanic acid (Sodium Salt)

The title compound was prepared from 1-benzyl-2-methyl-3-pyrazolin-5-one-4-carboxylic acid obtained in (c) above in a manner analogous to Example 4. The free acid possessed δ(CD$_3$OD) 1.47, 1.56 (2×3H, 2s, gem dimethyls), 3.56 (3H, s, —NMe), 4.30 (1H, s, C$_3$ penicillin proton), 5.20 (2H, s, PhCH$_2$N), 5.43 (1H, d, J4 Hz C$_5$ proton), 5.58 (1H, d, J4 Hz, C$_6$ proton), 5.80 (1H, s, —CH—CONH—), 7.30 (10H, m, aromatic protons), 8.04 (1H, s, pyrazole proton). The free acid was converted to the sodium salt by precipitation from an acetone solution of the free acid by addition of sodium ethyl hexanoate in methyl isobutyl ketone (1 equivalent 2M solution).

The sodium salt possessed $\nu_{max}$ (nujol) 1770 cm$^{-1}$.

MIC against *E.Coli* NCTC 10418 5 µg/ml.

EXAMPLE 10

6β-[D,2-(2,3-Dimethyl-1-(4-bromophenyl)-3-pyrazolin-5-one-4-carbonyl amino)-2-phenyl]acetamido penicillanic acid (sodium salt)

(a) 3-Methyl-1-(4-bromophenyl)-2-pyrazolin-5-one-4-

Bromophenyl hydrazine (3.069 g, 16.5 mmol) in glacial acetic acid (10 ml) was treated with ethyl acetoacetate (2.1 ml, 16.5 mmol) and the whole refluxed for 5 hours under nitrogen. On cooling the title product precipitated out and was filtered and washed with hexane (2.931 g, 70%) $\delta_{max}$(CHCl$_3$) 1710, 1585, 1480, 1620 cm$^{-1}$, $\delta$(CDCl$_3$) 2.20 (3H, s, C$_3$Me), 3.45 (2H, s, C$_4$ ring protons), 7.47 (2H, d, J9 Hz, 2 aryl protons), 7.83 (2H, d, J9 Hz, 2 aryl protons). Found: M$^+$, 251.9893; C$_{10}$H$_9$N$_2$OBr requires M, 251.9897.

(b) 2,3 Dimethyl-1-(4-bromophenyl)-3-pyrazolin-5-one

The title compound was prepared from 3-methyl-1-(4-bromophenyl)-2-pyrazolin-5-one obtained in (a) above in a manner analogous to example (8b). The title compound possessed $\delta_{max}$(CHCl$_3$) 1655, 1585, 1485 cm$^{-1}$, $\delta$(D$_6$Acetone) 2.28 (3H, s, C$_3$Me), 3.11 (3H, s, NMe), 5.28 (1H, s, C$_4$ proton), 7.32 (2H, d, J9 Hz) 2 aryl protons), 7.61 (2H, d, J9 Hz, 2 aryl protons). Found: M$^+$, 266.0040; C$_{11}$H$_{11}$N$_2$OBr requires M, 266.0052.

(c) 6β-[D,2-(2,3 Dimethyl-1-(4-bromophenyl)-3-pyrazolin-5-one-4-carbonyl amino)-2-phenyl]acetamido penicillanic acid (sodium salt)

The title compounds was prepared from 2,3 dimethyl-1-(4-bromophenyl)-3-pyrazolin-5-one obtained as in (b) above in a manner analogous to example (8c). The free acid possessed $\delta$(CD$_3$OD) 1.47, 1.57 (2×3H, 2s gem dimethyls), 2.66 (3H, s, C$_3$ Me Pyrazole), 3.35 (3H, s, —NMe), 4.30 (1H, s, C$_3$ penicillin proton), 5.45 (2H, m, C$_5$, C$_6$ penicillin protons), 5.69 (1H, s, —CH—CONH—), 7.35 (7H, m, aryl protons), 7.70 (2H, d, $\overline{J8}$ Hz, aryl protons), 8.95 (1H, d, J7 Hz, —NH (slowly exchanges)), 9.58 (1H, d, J7 Hz —$\overline{NH}$, slowly exchanges). The free acid was converted to the sodium salt in a manner analogous to example 69d. The sodium salt possessed $\nu_{max}$ (Nujol) 1770 cm$^{-1}$.

MIC against *E.Coli* NCTC 10418 5 µg/ml.

EXAMPLE 11

6β-[D,2-(2-(4-Nitrophenyl)-3-pyrazolin-5-one-4-carbonyl amino)-2-phenyl] acetamido penicillanic acid (sodium salt)

(a) 4-Ethoxycarbonyl-2-(4-nitrophenyl)-3-pyrazolin-5-one

4-Ethoxycarbonyl-2-phenyl-3-pyrazolin-5-one (3.78 g, 16.3 mmol) in concentrated sulphuric acid (16 ml) was treated at 0° C. with nitric acid (d1.42, 0.95 ml, 16.3 mmol) in concentrated sulphuric acid (16 ml). The whole was then stirred for 1 hour at 0° C. and then added to an ice water slurry. The precipitate formed was then filtered, washed with water, and dried in vacuum (4.1 g). Recrystallisation from ethanol gave mp 190° C. (3.05 g) $\nu_{max}$ (Nujol) 1685, 1590, 1520, 1500 cm$^{-1}$ $\delta$ (D$_6$—DMSO) 1.32 (3H, t, J7 Hz, —OCH$_2$CH$_3$); 4.27(2H, q, J7 Hz —OCH$_2$CH$_3$), 8.09 (2H, d, J9.5 $\overline{Hz}$, 2 aryl protons), 8.40 (2H, d, J9.5 Hz, 2 aryl protons), 9.06 (1H, s, C$_3$ pyrazole proton). Found: M$^+$ 277.0702; C$_{12}$H$_{11}$N$_3$O$_5$ requires M, 277.0697

(b) 2-(4-Nitrophenyl)-3-pyrazolin-5-one-4-carboxylic acid

The ester prepared as in (a) above (300 mg, 1.08 mmol) in 0.5N sodium hydroxide (20 ml) was stirred under nitrogen at reflux for 1 hour. The reaction mixture was allowed to cool, washed with ethyl acetate and then acidified to pH 1.5. The aqueous solution was then extracted with ethyl acetate which on drying (MgSO$_4$) and evaporation followed by ether trituration produced the title compound (267 mg). $\nu_{max}$ (Nujol) 1680, 1615, 1499, 1580 cm$^{-1}$, $\delta$(CD$_3$OD+D$_6$DMSO) 8.30 (4H, ABq, J10 Hz, aryl protons), 8.86(1H, s, C$_3$ pyrazole proton). Found: M$^+$, 249.0386; C$_{10}$H$_7$N$_3$O$_5$ requires M, 249.0386.

(c) 6β-[D,2-(2-(4-Nitrophenyl)-3-pyrazolin-5-one-4-carbonylamino)-2-phenyl] acetamido penicillanic acid (Sodium Salt)

The title compound was prepared from 2-(4-nitrophenyl)-3-pyrazolin-5-one-4-carboxylic acid obtained in (b) above in a manner analogous to Example 6(b). The free acid possessed $\delta$(CD$_3$OD) 1.45, 1.53 (2×3H, 2s, gem dimethyls), 4.29 (1H, s, C$_3$- penicillin proton), 5.42, 5.54(2H, ABq, J4 Hz C$_5$ and C$_6$ penicillin protons), 5.76 (1H, S,—CHCONH), 7.40(5H, m, ampicillin phenyl protons), $\overline{7.91}$ (2H, d, J9 Hz, protons m-NO$_2$), 8.30 (2H, d, J9 Hz, protons o-NO$_2$), 8.60 (1H, s, C$_3$ pyrazole proton). The free acid was converted to the sodium salt as in Example 6(b). The sodium salt possessed $\nu_{max}$ (Nujol) 1765 cm$^{-1}$.

MIC against *E.Coli* NCTC 10418 2.5 µg/ml.

EXAMPLE 12

6β-[D,2-(2-(4-Aminophenyl)-3-pyrazolin-5-one-4-carbonylamino)-2-phenyl] acetamido penicillanic acid (sodium salt)

The title compound was obtained from 6β [D,2-(2-(4-nitrophenyl)-3-pyrazolin-5-one-4-carbonylamino)-2-phenyl] acetamido penicillanic acid sodium salt in a manner analogous to example 7. The sodium salt possessed $\delta$max (Nujol) 1760 cm$^{-1}$ $\nu$(D$_2$O) 1.25, 1.35 (2×3H, 2s, gem dimethyls), 4.10 (1H, s, C$_3$ proton of penicillin), 5.36 (2H, incidental singlet, C$_5$ and C$_6$), 5.50 1H, s, —CH CONH—), 6.71 (2H,d, protons o to NH$_2$), 7.35 (7H, $\overline{m}$, penicillin phenyl protons+pyrazole aryl protons $\overline{m}$—NH$_2$), 7.95 (1H, s, C$_3$ pyrazole proton). MIC against *E.coli* NCTC 10418 5 µg/ml.

EXAMPLE 13

6β-[D,2-(2-(4-Nitrophenyl)-3-pyrazolin-5-one-4-carbonyl amino)-2-(4-hydroxy phenyl)] acetamido penicillanic acid (sodium salt)

The free penicillanic acid of the title compound was prepared in the same manner as in Example 11(c), except that amoxycillin trihydrate was used in place of ampicillin. The free acid possessed $\delta$(CD$_3$OD) 1.50, 1.57(2×3H, 2s, gem dimethyls), 4.37 (1H, s, C$_3$ penicillin proton), 5.58 (2H, m, C$_5$ and C$_6$ penicillin protons), 5.78 (1H, s, —CH—CONH—), 6.85(2H, d, J9 Hz, 2 aryl protons), 7.43 $\overline{(2H}$, d, J9Hz 2 aryl protons), 7.85 (2H, d, J8Hz, 2 aryl protons), 8.30 (2H, d, J8Hz, 2 aryl protons), 8.61 (1H, s, C$_3$ pyrazole proton). The free acid was converted to the sodium salt in a manner analogous to example 6(b). The sodium salt possessed $\nu$max (Nujol) 1760, 1560 cm$^{-1}$. MIC against *E.coli* NCTC 10418 5 μg/ml.

EXAMPLE 14

6β-[D,2-(2-(4-Aminophenyl)-3-pyrazolin-5-one-4-carbonyl amino)-2-(4-hydroxy phenyl)] acetamido penicillanic acid (sodium salt)

The title compound was obtained from 6β-[D,2-(2-(4-nitrophenyl)-3-pyrazolin-5-one-4-carbonyl amino)-2-(4-hydroxyphenyl)] acetamido penicillanic acid sodium salt in a manner analogous to example 7. The sodium salt possessed $\nu$max (Nujol) 1760 cm$^{-1}$ δ(D$_2$O) 1.40, 1.47(2×3H, 2s, gem dimethyls), 4.17 (1H, s, C$_3$ penicillin proton), 5.45 (3H, incidental singlet, C$_5$ and C$_6$ protons, —CH—CONH—), 6.87 (4H, m, 4 aryl protons), 7.39 (4H, m, 4 aryl protons), 8.11 (1H, s, C$_3$ pyrazole protons). MIC against *E.coli* NCTC 10418 2.5 μg/ml.

EXAMPLE 15

6β-[D,2-(2-(4-Hydroxyphenyl)-3-pyrazolin-5-one-4-carbonyl amino)-2-phenyl] acetamido penicillanic acid (sodium salt)

(a) 2-(4-Aminophenyl)-4-ethoxycarbonyl-3 pyrazolin-5-one

4-Ethoxycarbonyl-2-(4-nitrophenyl)-3-pyrazolin-5-one (5.66 g, 20.43 mmol) in distilled tetrahydrofuran (250 ml) containing 10% Palladium|charcoal catalyst (1.13 g) was hydrogenated at atmospheric pressure for 1½ hours at 0° C. followed by 2 hours at room temperature. The catalyst was then removed by filtration through celite and the celite washed with tetrahydrofuran. The filtrate was then evaporated to dryness to yield the title compound (5.0 g) after trituration (Ether; hexane), $\nu$max (Nujol) 1693, 1675, 1630, 1599, 1585, 1290, 835, 775 cm$^{-1}$ δ(D$_6$-Acetone) 1.37 (3H, t, J7 Hz, —OCH$_2$CH$_3$), 3.10 (2H, bs, —NH$_2$), 4.36 (2H, q,J7Hz, —OCH$_2$CH$_3$), 6.80 (2H, d, J9Hz, protons o—NH$_2$), 7.53 (2H, d, J9 Hz, protons m—NH$_2$), 8.35 (1H, s, C$_3$ pyrazole proton). Found: M$^+$, 247.0954; C$_{12}$H$_{13}$N$_3$O$_3$ requires M, 247.0956.

(b) 4-Ethoxycarbonyl-2-(4-hydroxyphenyl)-3-pyrazolin-5-one

4-Ethoxycarbonyl-2-(4-amino phenyl)-3-pyrazolin-5-one (610 mg, 2.46 mmol) in 5N Sulphuric acid (90 ml) was stirred on a boiling water bath to give a solution. This was cooled to 0° C. and the colloidal precipitate formed treated with sodium nitrite (190 mg, 2.71 mmol) in water (2 ml). The whole was then allowed to stir for 2 hours at 0° C. under nitrogen and then added dropwise to boiling 5N sulphuric acid (30 ml) so as not to interrupt boiling. The solution was then allowed to cool and was extracted with ethyl acetate which, after drying (MgSO$_4$) and evaporation, gave the crude product (190 mg). This was purified by chromatography on silica (hexane; ethyl acetate) to give the desired product (101 mg) $\nu$max (KBr Disc) 1660, 1595, 1520, 1433, 1277, 1140 cm$^{-1}$, δ(D$_6$-Acetone) 1.33(3H, t, J7 Hz,—OCH$_2$CH$_3$), 3.30(1H, br), 4.33(2H,q,J7 Hz—OCH$_2$CH$_3$), 6.94 (2H, d, J9 Hz, protons o—OH), 7.65 (2H,d, J9 Hz, protons m—OH), 8.44 (1H, s, C$_3$ pyrazole proton), 8.75 (1H, brs); Found: M$^+$, 248.0773; C$_{12}$H$_{12}$N$_2$O$_4$ requires M, 248.0797. Calculated: C,58.1; H,4.8; N,11.3, Found: C, 58.3; H,5.1; N, 11.0

(c) 2-[4-Hydroxy phenyl]-3-pyrazolin-5-one-4-carboxylic acid

The title compound was obtained from 4-ethoxycarbonyl-2-(4-hydroxyphenyl)-3-pyrazolin-5-one in an analogous manner to Example 11(b). The acid possessed δ (D$_6$—DMSO+CD$_3$OD) 6.88(2H,d, J9 Hz, protons o—OH), 7.56 (2H,d, J9 Hz, protons m—OH), 8.37(1H,s,C$_3$ pyrazole proton).

(d) 6β-[D,2-[2-[4-Hydroxyphenyl]-3-pyrazolin-5-one-4-carbonyl amino)-2-phenyl] acetamido penicillanic acid (sodium salt)

The acid prepared as described above in (c) (148 mg, 0.672 mmol) in dry dichloromethane (8 ml) containing dry dimethylformamide (2 drops) was treated at room temperature with triethylamine (94 μl, 0.672 mmol) to give a solution which was cooled to −20° C. and treated with thionylchloride (54 μl 0.73 mmol) in dry dichloromethane (1 ml). The whole was then stirred at −20° C. for 5 minutes and then chlorotrimethyl silane (171 μl, 1.34 mmol) in dry dichloromethane (1 ml) was added, followed by triethylamine (188 μ1, 1.34 mmol).

Simultaneously Ampicillin (235 mg, 0.672 mmol) in dry dichloromethane (5 ml) was treated with triethylamine (188 μl, 1.34 mmol) and stirred at room temperature for 20 mins. to give a solution of the triethylamine salt.

The ampicillin solution was cooled to −60° C. and treated with the silylated acid chloride from above. The whole was then allowed to warm to room temperature and then stirred for 2 hours. The dichloromethane was removed by evaporation and ethanol added, followed by acidification (HCl) to pH2. This solution was stirred for 20 min. and the ethanol removed by evaporation. The residue was then partitioned between ethyl acetate and dilute sodium bicarbonate solution at pH 7.5. The aqueous layer was subsequently separated and acidified (HCl) to pH 1.5. This was then extracted with ethyl acetate to give after drying (MgSO$_4$) and evaporation the desired penicillin free acid (164 mg). The free acid possessed δ(D$_6$ Acetone+D$_2$O) 1.48, 1.57 (2×3H, 2s, gemdimethyls), 4.35 (1H, s, C$_3$ penicillin proton), 5.67 (2H, ABq, J4 Hz, C$_5$ and C$_6$ penicillin protons), 6.03 (1H, s, —CH—CONH—), 6.98 (2H, d, J9 Hz, 2 aryl protons), 7.55 (7H, m, 7 aryl protons), 8.50 (1H, s, C$_3$ pyrazole proton). The free acid was converted to the sodium salt in a manner analogous to example 6, $\nu_{max}$ (Nujol) 1780 cm$^{-1}$.

MIC against *E.coli* NCTC 10418 2 μg/ml.

EXAMPLE 16

6β-[D,2-(3-Methyl-2-phenyl-3-pyrazolin-5-one-4-carbonyl-amino)-2-phenyl]acetamido penicillanic acid, sodium salt

(a) 4-Ethoxycarbonyl-3-methyl-2-phenyl-3-pyrazolin-5-one

Phenyl β-acetyl hydrazide (6.0 g, 40 mmol) in phosphorous trichloride (100 ml) was treated with diethyl acetomalonate (3.7 ml, 40 mmol) and the whole refluxed for 90 minutes. The mixture was then cooled, poured into ice-water and stirred for 10 minutes. The pH of the solution was adjusted to 4.0 with diluted sodium hydroxide solution while cooling with ice. Extraction with ethyl acetate followed by drying ($Na_2SO_4$) and evaporation of the organic solution gave a mixture of compounds from which the title product was isolated by chromatography on silica (hexane ethyl acetate) (0.14 g). Recrystallisation from aqueous ethanol gave prisms, mp 125°, $\nu_{max}$ ($CH_2Cl_2$) 3330, 1720, 1670 $cm^{-1}$, $\lambda_{max}$ (EtOH) 262 nm, $\delta((CD_3)_2CO)$ 1.38 (3H, t, J7 Hz, $CH_3$—C—O), 2.53 (3H, s, $CH_3$—C≡), 4.41 (2H, q, J7 Hz, —$CH_2$—O), 7.58 (5H, s, aryl protons), 8.83 (1H, br, —NH—).

Found: $M^+$, 246.1013 $C_{13}H_{14}N_2O_3$ requires M, 246.1003.

(b) 3-Methyl-2-phenyl-3-pyrazolin-5-one-4-carboxylic acid

The ethyl ester obtained in (a) above (0.14 g, 0.57 mmol) in ethanol (2 ml) was treated with 0.5 N NaOH solution (3.3 ml) and the solution refluxed for 5½ hours. The solution was cooled, acidified to pH 1.5 (5 N HCl) and extracted with ethyl acetate. Drying ($Na_2SO_4$) and evaporation of the organic layer gave the title product (0.11 g), purified by trituration with ether (0.10 g, 81%). It possessed $\delta$ (($CD_3)_2CO$) 2.54 (3H, s, $CH_3$—), 7.58 (5H, s, aryl protons), 8.3 (2H, —NH— and —$CO_2H$, broad).

(c) 6β-[D,2-(3-Methyl-2-phenyl-3-pyrazolin-5-one-4-carbonylamino)-2-phenyl] acetamido penicillanic acid, sodium salt The pyrazolinone acid obtained in (b) (0.10 g, 0.46 mmol) in dry dichloromethane (5 ml) was treated with triethylamine (0.10 ml, 0.7 mmol) and the solution cooled to −20° and treated with thionyl chloride(0.040 ml, 0.56 mmol) in dichloromethane (0.5 ml). The solution was then stirred 30 min. at −10°. Anhydrous ampicillin (0.15 g., 0.43 mmol) in dichloromethane (5 ml) was meanwhile separately treated with triethylamine (0.07 ml, 0.5 mmol); the suspension was stirred 20 mins. when further triethylamine (0.06 ml) was added to give a solution. This was cooled to 0° and the above pyrazolinone solution added dropwise. The whole was stirred 90 mins. at room temperature; 1 drop of 5 N HCl was added, the solution concentrated to low volume, ethyl acetate and water were added and the pH of the aqueous layer adjusted to 7.5 with sodium bicarbonate solution. The aqueous layer was separated, acidified to pH 1.5 (5 N HCl) and extracted with ethyl acetate. Drying ($Na_2SO_4$) and evaporation of the organic layer gave a crude product which was triturated with ethyl acetate (0.5 ml) to leave the desired title product as the solid free penicillanic acid (10 mg.) $\delta$ (($CD_3)_2CO+D_2O$) 1.49, 1.55 (2×3H, 2s, ($CH_3)_2$), 2.54 (3H, s, $CH_3$—C≡), 4.29 (1H, s, $C_3$-penicillanic proton), 5.56 (2H, m, $C_5$ and $C_6$-penicillanic protons), 5.89 (1H, s, —CH—CON—), 7.58 (11 H, complex, aryl and ring NH protons), 8.14 (partially exchanged —C—NH—CO). The free acid was converted to the sodium salt by suspension in water, addition of dilute sodium bicarbonate solution until, on shaking, dissolution occurred at pH 6.5, and freeze-drying.

MIC against *E.coli* NCTC 10418 25 μg/ml.

EXAMPLE 17

6β-[D,2-(2-p-βBromophenyl-3-pyrazolin-5-one-4-carbonylamino)-2-phenyl]acetamido penicillanic acid, sodium salt (a) 2-p-βBromophenyl-4-ethoxycarbonyl-3-pyrazolin-5-one p-βBromophenyl β-acetyl hydrazide (0.23 g., 1 mmol) in dry ethanol (5 ml) and concentrated $H_2SO_4$ ( 4 drops) was treated with diethyl ethoxymethylene malonate (0.216 ml., 1 mmol) and the solution refluxed for 5 hours. The solution was neutralised with sodium bicarbonate solution and the ethanol evaporated. The residue was partitioned between aqueous potassium carbonate solution and ethyl acetate. The aqueous layer was shaken, separated, acidified (5 N HCl) to pH 2.5 and extracted with ethyl acetate. Drying ($Na_2SO_4$) and evaporation gave a residue from which the title product (45 mg) was obtained by recrystallisation from aqueous ethanol (mp 138°), $\nu_{max}$ (nujol) 3130, 1720, 1690 $cm^{-1}$, ($CDCl_3$) 1.38 (3H, t, J 7 Hz, $CH_3$—), 4.38 (2H, t, 7 Hz, —$CH_2$), 7.55 (4H, br s, aryl protons), 8.10 (1H, s, pyrazole proton). $\lambda_{max}$ (EtOH) 284 nm ($E_m$ 18766).

(b) 2-p-βBromophenyl-3-pyrazolin-5-one-4-carboxylic acid

The ester prepared as described in (a) (90 mg., 0.29 mmol) was heated to reflux in 0.25 N sodium hydroxide solution (8 ml) for 1 h. Cooling, acidification (5 N HCl) to pH2 and ethyl acetate extraction, followed by drying ($Na_2SO_4$) and evaporation of the organic extract gave the title product (75 mg, 91%), $\delta((CD_3)_2SO)$ 7.70 (4H, ABq, J 9 Hz, aryl protons), 8.61 (1H, s, pyrazole proton).

(c) 6β-[D,2-(2-p-Bromophenyl-3-pyrazolin-5-one-4-carbonylamino)-2-phenyl]acetamido penicillanic acid, sodium salt The pyrazole acid prepared in (b) above (75 mg, 0.26 mmol) in dry methylene chloride (3 ml) with triethylamine (0.047 ml, 0.33 mmol) was cooled to −20° and treated with thionyl chloride (0.021 ml, 0.29 mmol) in methylene chloride (0.5 ml). The solution was stirred 30 min. at −5° when infrared analysis showed $\nu_{max}$ 1760 $cm^{-1}$. Ampicillin (0.09 g, 0.26 mmol) in dry methylene chloride (5 ml) with triethylamine (0.07 ml, 0.5 mmol) was stirred till dissolution occured. The solution was cooled to 0° and the above pyrazole solution added. The mixture was stirred 2 hours at room temperature. Water and ethyl acetate were added and the pH was raised to 7.5 with sodium bicarbonate solution. The aqueous layer was separated, acidified to pH 1.5 and extracted with ethyl acetate. Drying ($Na_2SO_4$) and evaporation gave the crude title product (30 mg). This material was chromatographed on silica (ethyl acetate (5): isoprophyl alcohol (4): water (1)). Silica residue was then removed by covering the desired column fractions with water, acidification to pH2 (HCl), and extraction with ethyl acetate. Drying ($Na_2SO_4$) and evaporation gave purified title product (15 mg), $\delta((CD_3)_2CO)$ 1.5 2,1.59(2×3H,2s, ($CH_3)_2$), 4.33 (1H,s,$C_3$-penicillanic proton). 5.50(1H,d,J4Hz, $C_5$-penicillanic proton), 5.56(1H,d,of d, J4, 10 Hz, $C_6$-penicillanic proton), 5.97 (1H,d,J8 Hz,—CH—CON—), 7.40(5H,complex, aryl protons), 7.68(4H,s, aryl(pyrazole)protons), 8.27

(2H,2d, J8,10 Hz,—NH—), 8.67(1H,s,pyrazole proton). The free acid was dissolved in water by the addidition of dilute sodium bicarbonate solution to pH 5.6 and shaking. Freeze-drying gave the sodium salt. M.I.C. against *E.coli* NCTC 10418 1.0 μg/ml.

EXAMPLE 18

7β-[D,2-(2-p-Nitrophenyl-3-pyrazolin-5-one-4-carbonyl-amino)-2-phenyl]acetamido-3-acetoxymethylceph-3-em-4-carboxylic acid, sodium salt 2-p-Nitrophenyl-3-pyrazolin-5-one-4-carboxylic acid, prepared as described in example 11(b) (0.10 g., 0.4 mmol) in dichloromethane (5 ml) was treated with triethylamine (0.08 ml, 0.57 mmol) and the solution cooled to −20° and treated with thionyl chloride (0.033 ml, 0.46 mmol) in dichloromethane (0.5 ml). The mixture was stirred 30 mins. at −10° and then added to a preformed solution of cephaloglycine triethylamine salt (0.42 mmol) and additional triethylamine (0.007 ml, 0.5 mmol) in dichloromethane (10 ml), at 0°. The solution was stirred 90 mins. at room temperature, concentrated and partitioned between ethyl acetate and dilute sodium bicarbonate solution (pH 7.5). The aqueous layer was separated, acidified to pH 1.5 (5N HCl) and extracted with ethyl acetate. Drying ($Na_2SO_4$) and evaporation gave the crude title product (0.18 g) as the free acid which was purified by chromatography on silica gel (ethyl acetate (5) : isopropyl alcohol (4) : water (1)). The product possessed δ (($CD_3)_2CO+D_2O$) 2.07 (3H, s, —$OCOCH_3$), 3.52 (2H, m, —$SCH_2$), 5.00 (3H, m, —$OCH_2$— and $C_6$-cephalosporinate proton), 5.96 (2H, m, CH—CON— and $C_7$-cephalosporinate proton), 7.46 (5H, m, aryl cephaloglycine derived protons), 8.20 (4H, ABq, J 8 Hz, other aryl protons), 8.79 (1H, s, pyrazole proton). This material was converted to the sodium salt (55 mg) by taking up in water by the addition of dilute sodium bicarbonate solution to pH 5.5 and freeze-drying the resulting solution.

MIC against *E.coli* NCTC 10418 1.0 μg/ml.

EXAMPLE 19

7β-[D,2-(2-p-Aminophenyl-3-pyrazolin-5-one-4-carbonylamino)-2-phenyl]acetamido-3-acetoxymethyl-ceph-3-em-4-carboxylic acid, sodium salt 7β-[D,2-(2-p-Nitrophenyl-3-pyrazolin-5-one-4-carbonylamino)-2-phenyl]acetamido-3-acetoxymethyl-ceph-3-em-4-carboxylic acid sodium salt (45 mg) prepared as described in example 18 in water (2 ml) was hydrogenated at S.T.P. over 10% palladium on charcoal (45 mg) for 3 hours. The solution was filtered through celite, which was washed with water and the combined solution freeze dried to give the title product (25 mg), δ($D_2O$) 2.07 (3H, s, —$OCO.CH_3$), 3.68 (2H, m, —$SCH_2$), 5.03 (3H, m, —$OCH_2$— and $C_6$-cephalosporinate proton), 5.73 (2H, m, CH—CON— and $C_7$-cephalosporinate proton), 6.83 (2H, d, J 10 Hz, —$NH_2$ aryl protons), 7.51 (7H, complex, other aryl protons), 8.13 (1H, s, pyrazole proton).

MIC against *E.coli* NCTC 10418 5 μg/ml.

EXAMPLE 20

6β-[D,2-(2-[4-Methoxyphenyl]-pyrazol-3-in-5-one-4-carbonylamino)-2-phenyl]acetamido penicillanic acid, sodium salt

(a)

4-Ethoxycarbonyl-2-[4-methoxyphenyl]-3-pyrazolin-5-one

1-Acetyl-2-[4-methoxyphenyl]hydrazide (1.58g, 8.78mmol) and concentrated sulphuric acid (30 drops) in dry ethanol (40ml) were treated with diethyl ethoxymethylene malonate (1.89ml, 8.78mmol) and the whole stirred at 100° C. under nitrogen for 5 hours. The reaction solution was cooled, basified to pH 6 with sodium hydroxide solution (2.5N) and the ethanol removed by evaporation. The residue was then dissolved in ethyl acetate and extracted twice with dilute potassium carbonate solution. The two extracts were combined and acidified to pH 2.5 (5N HCl). Ethyl acetate extraction produced after drying ($MgSO_4$) and evaporation 675mg of a mixture consisting of 4-ethoxy carbonyl-2-[4-methoxyphenyl]-3-pyrazolin-5-one and 4-ethoxycarbonyl-1-[4-methoxypenyl]-3-pyrazolin-5-one. The mixture was columned (($SiO_2$), 2:1 Hexane/Ethyl acetate) to give 366mg of the title compound. Recrystallisation from Hexane/Ethyl acetate gave mp 125°–127°, νmax($CHCl_3$) 1685, 1585, 1515, 1255cm$^{-1}$, δ ($D_6$-Acetone) 1.32 (3H,t,J7 Hz, —$OCH_2CH_3$) 3.80(3H,s,—$OCH_3$ 4.30 (2H,q,J7 Hz, —$OCH_2CH_3$) 7.00(2H,d, J9 Hz, protons o to —OMe), 7.68(2H,d, J9 Hz, protons m to —OMe), 8.41(1H,s, $C_3$-pyrazole proton). Found: $M^+$; 262.0951; $C_{13}H_{14}N_2O_4$ requires M; 262.0954.

(b) 2-[4-Methoxyphenyl]-3-pyrazolin-5-one-4-carboxylic acid

The ester prepared as described above in (a) was converted to the title acid in a manner analogous to example 11(b). The acid possessed $ν_{max}$(nujol) 1690, 1670, 1599, 1580, 1575,cm$^{-1}$, δ($CH_3OD|D_6DMSO$) 3.78 (3H,s,—OMe), 7.00 (2H,d,J9 Hz, protons o to —OMe), 7.66 (2H,d,J9 Hz, protons m to —OMe), 8.45(1H,s, $C_3$-pyrazole proton). Found: $M^{30}$, 234.0639; $C_{11}H_{10}N_2O_4$ requires M,234.0641.

(c)

6β-[D,2-(2-[4-Methoxyphenyl]-pyrazol-3-in-5-one-4-carbonylamino)-2-phenyl] aetamido penicillanic acid, sodium salt The acid obtained from (b) above (118mg, 0.5 mmol) in dry dichloromethane (4 ml) was treated with triethylamine (70 ul, 0.5 mmol) and stirred in solution under nitrogen. The solution was cooled to −30° C. and treated with thionylchloride (40 ul, 0.55 mmol) in dry dichloromethane (1 ml). After stirring for 20 mins at −30° C. a precipitate formed which was treated with chlorotrimethylsilane (64 ul, 0.5 mmol) in dry dichloromethane (1 ml) and triethylamine (70 ul, 0.5 mmol) to give a clear solution. Simultaneously ampicillin (175 mg, 0.5 mmol) in dry dichloromethane (5 ml) was treated with triethylamine (140 ul, 1 mmol) and stirred at room temperature till dissolution occured. The ampicillin solution was cooled to −30° C. and treated with the silylated acid chloride from above and the whole then allowed to warm to room temperature and stirred for 2 hours. The dichloromethane was removed by evaporation and acidic ethanol added to the residue followed by stirring for 20 mins. The excess ethanol was removed by evaporation and the residue partoned between ethyl acetate and dilute sodium bicarbonate solution at pH 7.5. The aqueous layer was separated, acidified to pH 1.5 (5NHCl) and extracted with ethyl acetate which on drying (Mg SO$_4$) and evaporation produced the title penicillin free acid (92 mg). This was converted to the sodium salt in a manner analogous to example 2, $\nu$max (Nujol) 1760 cm$^{-1}$. The free acid possessed 6(D$_6$ Acetone+D$_2$O) 1.48, 1.57 (2×3H, 2s, gemdimethyls), 3.81 (3H, s, —OMe), 4.33 (1H, s, C$_3$-penicillin proton), 5.62 (2H, ABq, J4Hz, C$_5$ and C$_6$ protons), 6.04 (1H, s, —CHCON—), 7.03 (2H, d, J1 0Hz, protons m to —OMe), 7.55, m, ampicillin phenyl protons and protons o to —OMe), 8.53 (1H, s, C$_3$-pyrazole proton).

MIC against E.coli NCTC 10418 0.25 μg/ml.

EXAMPLE 21

6-β-[D,2-([1H]-3-Methoxy-1-[4-nitrophenyl]pyrazole-4-carbonylamino)-2-phenyl]acetamido penicillanic acid, sodium salt (a)
[1H]-4-Ethoxycarbonyl-3-methoxy-1-[4-nitrophenyl]-pyrazole The title compound was prepared from 4-ethoxycarbonyl-2-[4-nitrophenyl]-3-pyrazolin-5-one in a manner analogous to example 5(a). The title compound possessed $\nu$max (Nujol) 1685, 1570, 1510, 1405, 1290 cm$^{-1}$, δ(D$_6$-DMSO) 1.45 (3H,t, J7 Hz, —OCH$_2$CH$_3$), 4.19 (3H, s, —OMe), 4.44 (2H, q, J7 Hz, —OCH$_2$CH$_3$), 8.53 (4H, ABq, J10 Hz, aryl protons), 9.39 (1H, s, C$_3$-pyrazole proton) Found: M +, 291.0861. C$_{13}$H$_{13}$N$_3$O$_5$ requires M,291.0855.

(b)
[1H]-[3-Methoxy-1-[4-nitrophenyl]pyrazole-4-carboxylic acid

The ester prepared as described above in (a) (288 mg, 0.98 mol) in 10% sodium hydroxide solution (10 ml) and methanol (6 ml) was stirred on a boiling water bath under nitrogen for 2.5 hours. The reaction mixture was removed from the water bath and the hot solution acidified (5N HCl) to pH 1.5. On cooling a precipitate formed which was extracted into ethyl acetate to give after drying (MgSO$_4$) and evaporation the title product (258mg) $\nu_{max}$(Nujol) 1710, 1675, 1599, 1580,cm$^{-1}$ δ(D$_6$—DMSO+CD$_3$OD) 4.01(3H,s,—OMe), 8.05 (2H,d,J10 Hz, protons m to—NO$_2$), 8.37 (2H,d,J10 Hz, protons o to —NO$_2$), 8.93 (1H,s,C$_3$-pyrazole proton). Found: M+,263.0541. C$_{11}$H$_9$O$_5$N$_3$ requires M, 263.0542.

(c)6δ-[D,2-([1H]-3-Methoxy-1-[4-nitrophenyl]pyrazole-4-carbonylamino)-2-phenyl]acetamido penicillanic acid, sodium salt The title compound was prepared from [1,H]-3-methoxy-1-[4-nitrophenyl]pyrazole-4-carboxylic acid, obtained in (b) above, in a manner analogous to example 5(c). The free acid possessed δ(D$_6$Acetone +D$_2$O) 1.48, 1.57(2×3H,2s, gem dimethyls), 4.16 (3H,s,—OMe), 4.35 (1H,s,C$_3$-penicillin proton), 5.67 (2H,ABq, J4 Hz, C$_5$ and C$_6$-penicillin protons), 6.03(1H,s,—CHCON—), 7.43(5H,m, ampicillin phenyl protons), 7.97(2H,d,J9 Hz, protons m to o—NO$_2$) 8.36(2H,d,J9 Hz, protons o to —NO$_2$) 8.82(1H,s,C$_3$-pyrazole proton). The free acid was converted to the sodium salt in a manner analogous to example 1. The sodium salt possessed $\nu_{max}$ (Nujol) 1760cm$^{-1}$.

MIC against E. coli NCTC 10418 8 μg/ml.

EXAMPLE 22

6β-[D,2-([1H]-1-(4-Aminophenyl)-3-methoxy pyrazole-4-carbonylamino)-2-phenyl]acetamido penicillanic acid, sodium salt The title compound was prepared from 6β-[D,2-([1H]-3-methoxy-1-(4-nitrophenyl) pyrazole-4-carbonylamino)-2-phenyl] acetamido penicillanic acid, sodium salt obtained in example 21(c), in a manner analogous to example 7. The sodium salt possessed $\nu_{max}$ (Nujol) 1760cm$^{-1}$ δ(D$_2$O) 1.38, 1.43(2×3H,2s, gem-dimethyls), 3.86 (3H,s,—OMe), 4.14(1H,s, C$_3$-penicillin proton), 5.42(2H,s, C$_5$ and C$_6$-penicillin protons), 5.48(1H,s,—CH—CON—), 6.73(2H,d,protons o to —NH$_2$), 7.18(2H,d,protons m to —NH$_2$), 7.41(5H,m, ampicillin phenyl protons), 7.95 (1H,s,C$_3$-pyrazole proton).

MIC against E.coli NCTC 10418 16 μg/ml.

EXAMPLE 23

6β-[D,2-(2-[4-Methylphenyl]pyrazol-3-in-5-one-4 carbony lamino)-2-phenyl]acetamido penicillanic acid, sodium salt (a) 1-Acetyl-2-[4-Methylphenyl]hydrazide (4-Methylphenyl)hydrazine (1.146 g, 9.38 mmol) in glacial acetic acid (25 ml) was stirred under nitrogen at reflux for 1.5 hours. The solution was allowed to cool and concentrated by evaporation. Addition of ether (5 ml) caused the title compound to precipitate out. This was then filtered and washed with 5:1 hexane/ether (1.324 g) $\nu_{max}$ (CHCl$_3$) 1685, 1615, 1510, 1460, 1220, cm$^{-1}$, δ(D$_6$Acetone) 1.97 (3H,s,-COCH$_3$), 2.23 (3H,s,p—CH$_3$), 6.90 (4H, ABq, J1 0Hz, aryl protons), 7.1 (1H,bs, —NH (exchangeable D$_2$O)) 9.06 (1H,bs,—NH (exchangeable D$_2$O)). Found: M$^+$, 164.0951; C$_9$H$_{12}$N$_2$O requires M; 164.0950.

(b)
4-Ethoxycarbonyl-2-(4-methylphenyl)-3-pyrazolin-5-one

1-Acetyl-2-[4-methylphenyl]hydrazide (328 mg, 2mmol) in phosphorous oxychloride (5 ml) was treated with diethylethoxy methylene malonate (432 ul, 2 mmol) and the whole stirred under nitrogen for 2 hours at 90° C. The reaction mixture was allowed to cool and then added dropwise to water (50 ml). The resultant solution was neutralised to pH 6 (NaOH) and then extracted with ether to give, after drying (MgSO$_4$) and evaporation, a mixture (385 mg) consisting of the title compound and 1-(1-chlorovinyl)-4-ethoxycarbonyl-2-(4-methylphenyl)-3-pyrazolin-5-one. The title compound was separated by column chromatography (SiO$_2$; 2:1 Hexane: Ethylacetate) (94 mg). $\nu_{max}$ (CHCl$_3$) 1720, 1680, 1580, 1510, 1120, cm$^{-1}$, δ(D$_6$Acetone) 1.35 (3H,t, J7 Hz, OCH$_2$CH$_3$), 2.38 (3H,s, p-CH$_3$), 4.34(2H,q, J7 Hz, —OCH$_2$CH$_3$), 7.50 (4H, ABq, J1 0Hz, aryl protons), 8.51(1H,s, C$_3$ pyrazole proton), 8.85 (1H,bs, —NH [exchangeable D$_2$O ]). Found: M$^+$-246.1006; C$_{13}$,H$_{14}$N$_2$O$_3$ requires M, 246.1003

(c) 2-(4-Methylphenyl)-3-pyrazolin-5-one-4-carboxylic acid

The ester prepared in (b) above (245 mg, 0.99 mmol) in 2.5N sodium hydroxide (5 ml) and ethanol (1 ml) was stirred at reflux under nitrogen for 0.75 hours. and then allowed to cool. The solution was washed with ethylacetate and then acidified to pH 1.5 (5 N HCl), whereupon the title compound precipitated out, was filtered and was washed with water. Drying in vacuum gave (183 mg). $\nu_{max}$(Nujol) 1655, 1580, 1525, 1325, 1140, 100, cm$^{-1}$. δ(CD$_3$OD+Drop D$_6$DMSO) 2.38 (3H,s, p-CH$_3$), 7.50 (4H, ABq, J9 Hz, aryl protons) 8.55 (1H,s,C$_3$ pyrazole proton). Found:M$^+$, 2.8.0696; C$_{11}$H$_{10}$N$_2$O$_3$ requires M,218.0691.

(d)6β-[D,2-(2-[4-Methylphenyl]pyrazol-3-in-5-one-4-carbonylamino)-2-phenyl] acetamido penicillanic acid, sodium salt The title compound was prepared from 2-(4-methylphenyl)-3-pyrazolin-5-one-4-carboxylic acid in a manner analogous to example 1. The free acid possessed δ(D$_6$Acetone+D$_2$O) 1.50, 1.59 (2×3H,2s, gem dimethyl), 2.37 (3H,s, p-CH$_3$), 4.34 (1H,s,C$_3$-penicillin proton), 5.75 (3H,m, CHCON—; C$_5$ and C$_6$-penicillin protons), 7.50 (9H,m, aryl protons), 8.65(1H,s,C$_3$-pyrazole proton). The free acid was converted to the sodium salt in a manner analogous to example 2. The sodium salt possessed $\nu_{max}$ (Nujol) 1760 cm$^{-1}$.

MIC against *E.coli* NCTC 10418 10 μg/ml.

EXAMPLE 24

6β-[D,2-(2-(-p-4-Hydroxy-n-butyl-1-amino)phenyl pyrazol-3-in-5-one-4-carbonylamino)-2-phenyl] acetamido penicillanic acid, sodium salt (a) 2-(p-4-Hydroxy-n-butyl-1-amino)phenyl pyrazol-3-in-5-one-4-carboxylic acid 4-Ethoxycarbonyl-2-(p-4-hydroxy-n-butyl-1-amino) phenyl pyrazol-3-in-5-one (120 mg, 0.38 mmol) in 0.5N sodium hydroxide solution (3ml) was heated on a water bath for 90 mins. The solution was cooled, acidified (5NHCl) to pH 3.5 and extracted with ethyl acetate to give, on drying and evaporation, the title product (50 mg) δ(CD$_3$OD) 1.63(4H,m, C—(CH$_2$)$_2$—C), 3.09(2H,m,—NCH$_2$—), 3.53(2H,m,CH$_2$O—), 6.57(2H,d,J9Hz, aryl protons), 7.29(2H,d,J9Hz, aryl protons), 8.07 (1H,s, pyrazole proton).

(b) 6β-[D,2-(2-(p-4-Hydroxy-n-butyl-1-amino) phenyl pyrazol-3-in-5-one-4-carbonylamino)-2-phenyl] acetamido penicillanic acid, sodium salt The acid prepared in (a) above (50 mg, 0.17 mmol) in methylene chloride (5 ml) with triethylamine (0.03 ml, 0.21 mmol) was cooled to −20° and treated with thionyl chloride (0.013ml, 0.18mmol) in methylene chloride (0.5 ml). After 10 mins. at −10°, trimethylsilyl chloride (0.042 ml, 0.33mmol) in methylene chloride (0.5 ml) was added, followed by triethylamine (0.047 ml, 0.33 mmol). This mixture was stirred 2 mins at −20° and then added to pre-dissolved ampicillin (0.06 g, 0.17 mmol) with triethylamine (0.05 ml, 0.35 mmol) in methylene chloride (3 ml) at 0°. The solution was stirred 2 hours at room temperature and then partitioned between aqueous sodium bicarbonate solution at pH 7.5 and excess ethyl acetate. The aqueous layer was separated and acidified to pH 1.5(5 NHCl) Ethyl acetate extraction, followed by drying and evaporation gave the title product (20 mg) as the free acid δ(CD$_3$OD) 1.45, 1.54(6H,2s,(CH$_3$)$_2$), 1.65(4H,m,—C—(CH$_2$)$_2$—C—1), 3.08(2H,m,—NCH$_2$—), 3.54(2H,m,-OCH$_2$), 4.24(1H,s,C$_3$—proton), 5.32(1H,d,J4Hz,C$_5$-proton), 5.44 (1H,d,J4Hz, C$_6$-proton), 5.67(1H,sα-proton), 6.58(2H,d, J9Hz, aryl protons), 7.24(7H, complex, aryl protons), 8.03(1H,s,pyrazole proton). This was converted to the sodium salt in the usual way (bicarbonate:-freeze-drying).

We claim:

1. A compound of formula (I) or a pharmaceutically acceptable salt or in-vivo hydrolysable ester thereof:

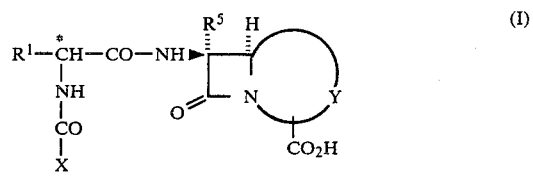

wherein R$^1$ is phenyl, substituted phenyl or a 5- or 6-membered heterocyclic ring containing up to three heteroatoms selected from the group consisting of oxygen, sulphur and nitrogen, optionally substituted with hydroxy, amino, halogen or alkoxy of 1 to 6 carbon atoms; X represents

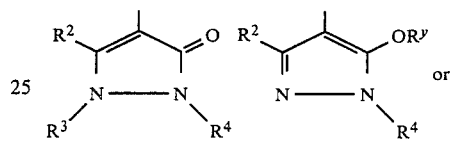

wherein R$^y$ is methyl or acetyl; R$^2$ and R$^3$ may be the same or different and each is hydrogen, an aryl group, a heterocyclyl group or an alkyl group of 1 to 6 carbon atoms optionally substituted by an aryl group or a heterocyclyl group; and R$^4$ is hydrogen, an alkylcarbonyl group of 1 to 6 carbon atoms in the alkyl moiety, an aryl group, a heterocyclyl group, an alkyl group of 1 to 6 carbon atoms optionally substituted by an aryl group or a heterocyclyl group; R$^5$ represents hydrogen, methoxy or —NHCHO; and Y is:

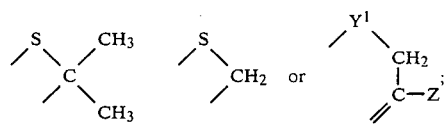

wherein Y$^1$ is oxygen, sulphur or —CH$_2$— and Z represents hydrogen, halogen, alkoxy of 1 to 4 carbon atoms, —CH$_2$Q or —CH═CH—Q wherein Q represents hydrogen, halogen, hydroxy, mercapto, cyano, carboxy, carbamoyloxy carboxylic ester, alkyloxy of 1 to 4 carbon atoms, acyloxy, aryl, a heterocyclyl group bonded via carbon, a heterocyclylthio group or a nitrogen containing heterocyclic group bonded via nitrogen and the carbon atom marked * is asymmetric.

2. A compound as claimed in claim 1 wherein Y is —S—C(CH$_3$)$_2$— or —S—CH$_2$—C(CH$_2$Q)═.

3. A compound as claimed in claim 1 wherein Y is —S—C(CH$_3$)$_2$—.

4. A compound as claimed in claim 1 wherein R$^5$ is hydrogen.

5. A compound as claimed in claim 1 of formula (II) or a pharmaceutically acceptable salt or in-vivo hydrolysable ester thereof:

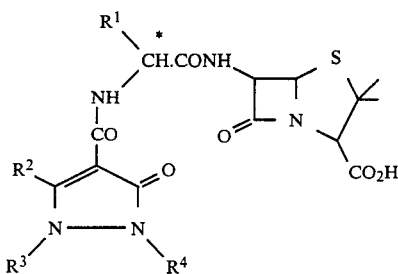

wherein R¹ is phenyl, substituted phenyl or a 5- or 6-membered heterocyclic ring containing up to three heteroatoms selected from the group consisting of oxygen, sulphur and nitrogen optionally substituted with hydroxy, amino, halogen or alkoxy of 1 to 6 carbon atoms; R² and R³ may be the same or different and each is hydrogen, an aryl group, a heterocyclyl group or an alkyl group of 1 to 6 carbon atoms optionally substituted by an aryl group or a heterocyclyl group; and R⁴ is hydrogen, an alkylcarbonyl group of 1 to 6 carbon atoms in the alkyl moiety, an aryl group, a heterocyclyl group, an alkyl group of 1 to 6 carbon atoms optionally substituted by an aryl group or a heterocyclyl group; and the carbon atom marked * is asymmetric.

6. A compound as claimed in claim 1 selected from the following or a pharmaceutically acceptable salt or in vivo hydrolysable ester thereof:

(a)
6β-[D,2-(2,3-dimethyl-1-phenyl-3-pyrazolin-5-one-4-carbonylamino)-2-phenyl]acetamido penicillanic acid;

6β-[D,2-(2,3-dimethyl-1-phenyl-3-pyrazolin-5-one-4-carbonylamino)-2-(4-hydroxyphenyl)]acetamido penicillanic acid;

6β-[D,2-(2-phenyl-3-pyrazolin-5-one-4-carbonylamino)-2-phenyl]acetamido penicillanic acid; and (b) 6β-[D,2-(2H,3-Hydroxy-2-phenyl pyrazole-4-carbonyl amino)-2-phenyl] acetamido penicillanic acid;

6β-[D,2-(2H,3-Methoxy-2-phenylpyrazole-4-carbonylamino -2-phenyl] acetamido penicillanic acid;

6β-[D,2-(2-Ethyl-3-methyl-1-(4-nitrophenyl)-3-pyrazolin-5-one-4-carbonyl amino)-2-phenyl] acetamido penicillanic acid;

6β-[D2,-(2-Ethyl-3-methyl-1-(4-aminophenyl)-3-pyrazolin -5-one-4-carbonylamino)-2-phenyl]acetamido penicillanic acid;

6β-[D,2-(2-Methyl-1-phenyl-3-pyrazolin-5-one-4-carbonyl amino)-2-phenyl]acetamido penicillanic acid;

6β-[D,2-(1-Benzyl-2-methyl-3-pyrazolin-5-one-4-carbonyl amino)-2-phenyl]acetamido penicillanic acid;

6β-[D,2-(2,3-Dimethyl-1-(4-bromophenyl)-3-pyrazolin-5-one-4-carbonyl amino)-2-phenyl]acetamido penicillanic acid;

6β-[D,2-(2-(4-Nitrophenyl)-3-pyrazolin-5-one-4-carbonyl amino)-2-phenyl]acetamido penicillanic acid;

6β-[D,2-(2-(4-Aminophenyl)-3-pyrazolin-5-one-4-carbonyl amino)-2-phenyl]acetamido penicillanic acid;

6β-[D,2-(2-(4-Nitrophenyl)-3-pyrazolin-5-one-4-carbonyl amino)-2-(4-hydroxy phenyl)]acetamido penicillanic acid;

6β-[D,2-(2-(4-Aminophenyl)-3-pyrazolin-5-one-4-carbonyl amino)-2-(4-hydroxy phenyl)]acetamido penicillanic acid;

6β-[D,2-(3-Methyl-2-phenyl-3-pyrazolin-5-one-4-carbonyl amino)-2-phenyl]acetamido penicillanic acid;

6β-[D,2-(4-Hydroxyphenyl-3-pyrazolin-5-one-4-carbonyl amino)-2-phenyl]acetamido penicillanic acid;

6β-[D,2-(2-p-Bromophenyl-3-pyrazolin-5-one-4-carbonyl amino)-2-phenyl]acetamido penicillanic acid;

7β-[D,2-(2-p-Nitrophenyl-3-pyrazolin-5-one-4-carbonylamino)-2-phenyl]acetamido-3-acetoxymethyl-ceph-3-em-4-carboxylic acid;

7β-[D,2-(2-p-Aminophenyl-3-pyrazolin-5-one-4-carbonyl amino)-2-phenyl]acetamido-3-acetoxymethyl-ceph-3-em-4-carboxylic acid;

6β-[D,2-(2-[4-Methoxyphenyl]-pyrazol-3-in-5-one-4-carbonylamino)-2-phenyl]acetamido penicillanic acid; and 6β-[D,2-([1H]-3-Methoxy-1-[4-nitrophenyl]pyrazole-4-carbonylamino)-2-phenyl]acetamido penicillanic acid; and 6β-[D,2-([1H]-1-(4-Aminophenyl)-3-methoxy pyrazole-4-carbonylamino)-2-phenyl]acetamido penicillanic acid; and 6β-[D,2-(2-[4-methylphenyl]pyrazol-3-in-5-one-4-carbonylamino)-2-phenyl]acetamido penicillanic acid: and 6β-[D,2-(2-p-4-hydroxy-n-butyl-1-amino)phenyl pyrazol-3-in-5-one-4-carbonylamino)-2-phenyl]acetamido penicillanic acid.

7. A pharmaceutical composition useful for treating bacterial infections in humans and animals which comprises an antibacterially effective amount of a compound of the formula (I) or a pharmaceutically acceptable salt or in-vivo hydrolysable ester thereof:

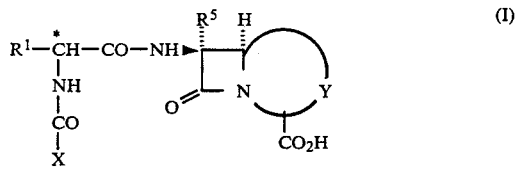

wherein R¹ is phenyl, substituted phenyl or a 5- or 6-membered heterocyclic ring containing up to three heteroatoms selected from the group consisting of oxygen, sulphur and nitrogen, optionally substituted with hydroxy, amino, halogen or alkoxy of 1 to 6 carbon atoms; X represents

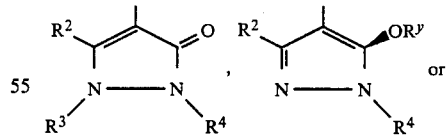

or

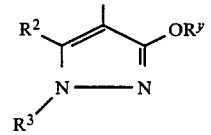

wherein $R^y$ is methyl or acetyl; R² and R³ may be the same or different and each is hydrogen, an aryl group, a heterocyclyl group or an alkyl group of 1 to 6 carbon atoms optionally substituted by an aryl group or a heterocyclyl group; and R⁴ is hydrogen, an alkylcarbonyl group of 1 to 6 carbon atoms in the alkyl moiety, an aryl group, a heterocyclyl group, an alkyl group of 1 to 6 carbon atoms optionally substituted by an aryl group or a heterocyclyl group; R⁵ represents hydrogen, methoxy or —NHCHO; and Y is:

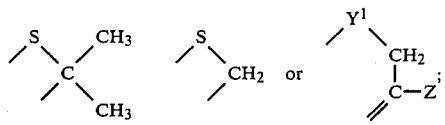

wherein Y¹ is oxygen, sulphur or —CH₂— and Z represents hydrogen, halogen, alkoxy of 1 to 4 carbon atoms, —CH₂Q or —CH=CH—Q wherein Q represents hydrogen, halogen, hydroxy, mercapto, cyano, carboxy, carbamoyloxy carboxylic ester, alkyloxy of 1 to 4 carbon atoms, acyloxy, aryl, a heterocyclyl group bonded via carbon, a heterocyclylthio group or a nitrogen containing heterocyclic group bonded via nitrogen and the carbon atom marked * is asymmetric, in combination with a pharmaceutically acceptable carrier.

8. A composition according to claim 7, wherein Y is —S—C(CH₃)₂— or —S—CH₂—C(CH₂Q)=.

9. A composition according to claim 7 wherein Y is —S—C(CH₃)₂—.

10. A composition according to claim 7 wherein R⁵ is hydrogen.

11. A composition according to claim 7 wherein the compound is of the formula (II) or a pharmaceutically acceptable salt or in-vivo hydrolysable ester thereof:

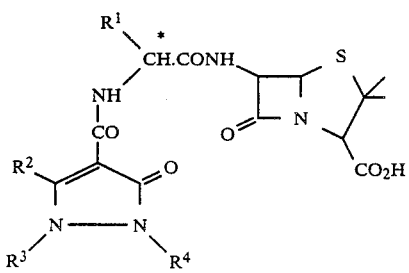

wherein R¹ is phenyl, substituted phenyl or a 5- or 6-membered heterocyclic ring containing up to three heteroatoms selected from the group consisting of oxygen, sulphur and nitrogen, optionally substituted with hydroxy, amino, halogen or alkoxy of 1 to 6 carbon atoms; R² and R³ may be the same or different and each is hydrogen, an aryl group, a heterocyclyl group or an alkyl group of 1 to 6 carbon atoms optionally substituted by an aryl group or a heterocyclyl group; and R⁴ is hydrogen, an alkylcarbonyl group of 1 to 6 carbon atoms in the alkyl moiety, an aryl group, a heterocyclyl group, an alkyl group of 1 to 6 carbon atoms optionally substituted by an aryl group or a heterocyclyl group; and the carbon atom marked * is asymmetric.

12. A composition according to claim 7, wherein the compound is selected from the following or a pharmaceutically acceptable salt or in vivo hydrolysable ester thereof:

(a)
6β-[D,2-(2,3-dimethyl-1-phenyl-3-pyrazolin-5-one-4-carbonylamino)-2-phenyl]acetamido penicillanic acid;

6β-[D,2-(2,3-dimethyl-1-phenyl-3-pyrazolin-5-one-4-carbonylamino)-2-(4-hydroxyphenyl)]acetamido penicillanic acid;

6β-[D,2-(2-phenyl-3-pyrazolin-5-one-4-carbonylamino)-2-phenyl]acetamido penicillanic acid; and 6β-[D,2-(3-Methyl-2-phenyl-3-pyrazolin-5-one-4-carbonyl amino)-2-phenyl]acetamido penicillanic acid;

6β-[D,2-(4-Hydroxyphenyl-3-pyrazolin-5-one-4-carbonyl amino)-2-phenyl]acetamido penicillanic acid;

6β-[D,2-(2-p-Bromophenyl-3-pyrazolin-5-one-4-carbonyl amino)-2-phenyl]acetamido penicillanic acid;

7β-[D,2-(2-p-Nitrophenyl-3-pyrazolin-5-one-4-carbonylamino)-2-phenyl]acetamido-3-acetoxymethyl-ceph-3-em-4-carboxylic acid;

7β-[D,2-(2-p-Aminophenyl-3-pyrazolin-5-one-4-carbonyl amino)-2-phenyl]acetamido-3-acetoxymethyl-ceph-3-em-4carboxylic acid;

6β-[D,2-(2-[4-Methoxyphenyl]-pyrazol-3-in-5-one-4-carbonylamino)-2-phenyl]acetamido penicillanic acid;

6β-[D,2-([1H]-3-Methoxy-1-[4-nitrophenyl]pyrazole-4-carbonylamino)-2-phenyl]acetamido penicillanic acid; and 6β-[D,2-([1H]-1-(4-Aminophenyl)-3-methoxy pyrazole-4-carbonylamino)-2-phenyl]acetamido penicillanic acid.

13. A method of treating bacterial infections in humans and animals which comprises administering to a human or animal in need thereof an antibacterially effective amount of a compound of the formula (I) or a pharmaceutically acceptable salt or in-vivo hydrolysable ester thereof:

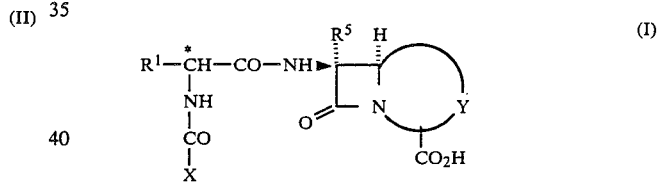

wherein R¹ is phenyl, substituted phenyl or a 5- or 6-membered heterocyclic ring containing up to three heteroatoms selected from the group consisting of oxygen, sulphur and nitrogen, optionally substituted with hydroxy, amino, halogen or alkoxy of 1 to 6 carbon atoms; X represents

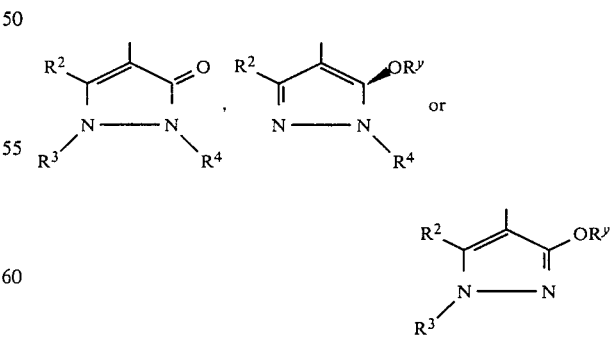

wherein R^y is methyl or acetyl; R² and R³ may be the same or different and each is hydrogen, an aryl group, a heterocyclyl group or an alkyl group of 1 to 6 carbon atoms optionally substituted by an aryl group or a heterocyclyl group; and R⁴ is hydrogen, an alkylcarbonyl group of 1 to 6 carbon atoms in the alkyl moiety, an aryl group, a heterocyclyl group, an alkyl group of 1 to 6 carbon atoms optionally substituted by an aryl group or a heterocyclyl group; $R^5$ represents hydrogen, methoxy or —NHCHO; and Y is:

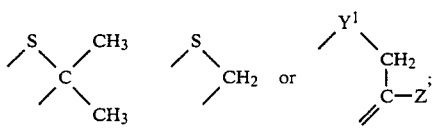

wherein $Y^1$ is oxygen, sulphur or —CH$_2$— and Z represents hydrogen, halogen, alkoxy of 1 to 4 carbon atoms, —CH$_2$Q or —CH=CH—Q wherein Q represents hydrogen, halogen, hydroxy, mercapto, cyano, carboxy, carbamoyloxy carboxylic ester, alkyloxy of 1 to 4 carbon atoms, acyloxy, aryl, a heterocyclyl group bonded via carbon, a heterocyclylthio group or a nitrogen containing heterocyclic group bonded via nitrogen and the carbon atom marked * is asymmetric, in combination with a pharmaceutically acceptable carrier.

14. A method according to claim 13 wherein Y is —S—C(CH$_3$)$_2$— or —S—CH$_2$—C(CH$_2$Q)=.

15. A method according to claim 13 wherein Y is —S—C(CH$_3$)$_2$—.

16. A method according to claim 13 wherein $R^5$ is hydrogen.

17. A method according to claim 13 wherein the compound is of the formula (II):

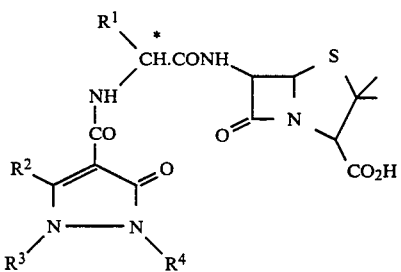

wherein $R^1$ is phenyl, substituted phenyl or a 5- or 6-membered heterocyclic ring containing up to three heteroatoms selected from the group consisting of oxygen, sulphur and nitrogen, optionally substituted with hydroxy, amino, halogen or alkoxy of 1 to 6 carbon atoms; $R^2$ and $R^3$ may be the same or different and each is hydrogen, an aryl group, a heterocyclyl group or an alkyl group of 1 to 6 carbon atoms optionally substituted by an aryl group or a heterocyclyl group; and $R^4$ is hydrogen, an alkylcarbonyl group of 1 to 6 carbon atoms in the alkyl moiety, an aryl group, a heterocyclyl group, an alkyl group of 1 to 6 carbon atoms optionally substituted by an aryl group or a heterocyclyl group; and the carbon atom marked * is asymmetric.

18. A method according to claim 13 wherein the compound is selected from the following or a pharmaceutically acceptable salt or in vivo hydrolysable ester thereof:

(a)

6β-[D,2-(2,3-dimethyl-1-phenyl-3-pyrazolin-5-one-4-carbonylamino) 2-phenyl]acetamido penicillanic acid;

6β-[D,2-(2,3-dimethyl-1-phenyl-3-pyrazolin-5-one-4-carbonylamino)-2-(4-hydroxyphenyl)]acetamido penicillanic acid;

6β-[D,2-(2-phenyl-3-pyrazolin-5-one-4-carbonylamino)-2-phenyl]acetamido penicillanic acid; and 6β-[D,2-(3-Methyl-2-phenyl-3-pyrazolin-5-one-4-carbonyl amino)-2-phenyl]acetamido penicillanic acid;

6β-[D,2-(4-Hydroxyphenyl-3-pyrazolin-5-one-4-carbonyl amino)-2-phenyl]acetamido penicillanic acid;

6β-[D,2-(2-p-Bromophenyl-3-pyrazolin-5-one-4-carbonyl amino)-2-phenyl]acetamido penicillanic acid;

7β-[D,2-(2-p-Nitrophenyl-3-pyrazolin-5-one-4-carbonylamino)-2-phenyl]acetamido-3-acetoxymethyl-ceph-3-em-4-carboxylic acid;

7β-[D,2-(2-p-Aminophenyl-3-pyrazolin-5-one-4-carbonyl amino)-2-phenyl]acetamido-3-acetoxymethyl-ceph-3-em-4-carboxylic acid;

6β-[D,2-(2-[4-Methoxyphenyl]-pyrazol-3-in-5-one-4-carbonylamino)-2-phenyl]acetamido penicillanic acid;

6β-[D,2-([1H]-3-Methoxy-1-[4-nitrophenyl]pyrazole-4-carbonylamino)-2-phenyl]acetamido penicillanic acid; and 6β-[D,2-([1H]-1-(4-Aminophenyl)-3-methoxy pyrazole-4-carbonylamino)-2-phenyl]acetamido penicillanic acid.

19. A pharmaceutical composition useful for treating bacterial infections in humans and animals which comprises an antibacterially effective amount of a compound of the formula (I) or a pharmaceutically acceptable salt or in-vivo hydrolysable ester thereof:

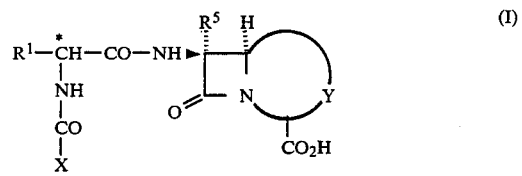

wherein $R^1$ is phenyl, substituted phenyl or a 5- or 6-membered heterocyclic ring containing up to three heteroatoms selected from the group consisting of oxygen, sulphur and nitrogen, optionally substituted with hydroxy, amino, halogen or alkoxy of 1 to 6 carbon atoms; X represents

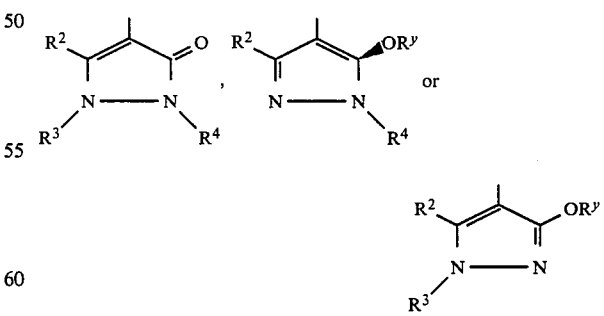

wherein $R^y$ is methyl or acetyl; $R^2$ and $R^3$ may be the same or different and each is hydrogen, an aryl group, a heterocyclyl group or an alkyl group of 1 to 6 carbon atoms optionally substituted by an aryl group or a heterocyclyl group; and $R^4$ is hydrogen, an alkylcarbonyl group of 1 to 6 carbon atoms in the alkyl moiety, an aryl group, a heterocyclyl group, an alkyl group of 1 to 6 carbon atoms optionally substituted by an aryl group or a heterocyclyl group; $R^5$ represents hydrogen, methoxy or —NHCHO; and Y is;

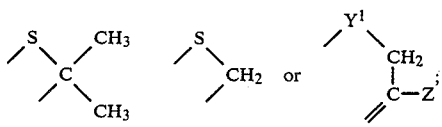

wherein $Y^1$ is oxygen, sulphur or —$CH_2$— and Z represents hydrogen, halogen, alkoxy of 1 to 4 carbon atoms, —$CH_2Q$ or —CH=CH—Q wherein Q represents hydrogen, halogen, hydroxy, mercapto, cyano, carboxy, carbamoyloxy carboxylic ester, alkyloxy of 1 to 4 carbon atoms, acyloxy, aryl, a heterocyclyl group bonded via carbon, a heterocyclylthio group or a nitrogen containing heterocyclic group bonded via nitrogen and the carbon atom marked * is asymmetric, and a beta-lactamase inhibitory amount of a beta-lactamase inhibitor, in combination with a pharmaceutically acceptable carrier.

20. A composition according to claim 18, wherein Y is —S—C($CH_3$)$_2$— or —S—$CH_2$—C($CH_2Q$)=.

21. A composition according to claim 18, wherein Y is —S—C($CH_3$)$_2$—.

22. A composition according to claim 18, wherein $R^5$ is hydrogen.

23. A composition according to claim 19 wherein the compound is of the formula (II) or a pharmaceutically acceptable salt or in-vivo hydrolysable ester thereof:

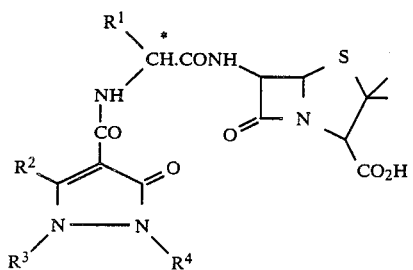

(II)

wherein $R^1$ is phenyl, substituted phenyl or a 5- or 6-membered heterocyclic ring containing up to three heteroatoms selected from the group consisting of oxygen, sulphur and nitrogen, optionally substituted with hydroxy, amino, halogen or alkoxy of 1 to 6 carbon atoms; $R^2$ and $R^3$ may be the same or different and each is hydrogen, an aryl group, a heterocyclyl group or an alkyl group of 1 to 6 carbon atoms optionally substituted by an aryl group or a heterocyclyl group; and $R^4$ is hydrogen, an alkylcarbonyl group of 1 to 6 carbon atoms in the alkyl moiety, an aryl group, a heterocyclyl group, an alkyl group of 1 to 6 carbon atoms optionally substituted by an aryl group or a heterocyclyl group; and the carbon atom marked * is asymmetric.

24. A composition according to claim 19, wherein the compound is selected from the following or a pharmaceutically acceptable salt or in vivo hydrolysable ester thereof:

(a)
6β-[D,2-(2,3-dimethyl-1-phenyl-3-pyrazolin-5-one-4-carbonylamino)-2-phenyl]acetamido penicillanic acid;

6β-[D,2-(2,3-dimethyl-1-phenyl-3-pyrazolin-5-one-4-carbonylamino)-2-(4-hydroxyphenyl)]acetamido penicillanic acid;

6β-[D,2-(2-phenyl-3-pyrazolin-5-one-4-carbonylamino)-2-phenyl]acetamido penicillanic acid; and 6β-[D,2-(3-Methyl-2-phenyl-3-pyrazolin-5-one-4-carbonyl amino)-2-phenyl]acetamido penicillanic acid;

6β-[D,2-(4-Hydroxyphenyl-3-pyrazolin-5-one-4-carbonyl amino)-2-phenyl]acetamido penicillanic acid;

6β-[D,2-(2-p-Bromophenyl-3-pyrazolin-5-one-4-carbonyl amino)-2-phenyl]acetamido penicillanic acid;

7β-[D,2-(2-p-Nitrophenyl-3-pyrazolin-5-one-4-carbonylamino)-2-phenyl]acetamido-3-acetoxymethyl-ceph-3-em-4-carboxylic acid;

7β-[D,2-(2-p-Aminophenyl-3-pyrazolin-5-one-4-carbonyl amino)-2-phenyl]acetamido-3-acetoxymethyl-ceph-3-em-4-carboxylic acid;

6β-[D,2-(2-[4-Methoxyphenyl]-pyrazol-3-in-5-one-4-carbonylamino)-2-phenyl]acetamido penicillanic acid;

6β-[D,2-([1H]-3-Methoxy-1-[4-nitrophenyl]pyrazole-4-carbonylamino)-2-phenyl]acetamido penicillanic acid; and 6β-[D,2-([1H]-1-(4-Aminophenyl)-3-methoxy pyrazole-4-carbonylamino)-2-phenyl]acetamido penicillanic acid:

6β-[D,2-(2-[4-methylphenyl]pyrazol-3-in-5-one-4-carbonylamino)-2-phenyl]acetamido penicillanic acid; and 6β-[D,2-(2-p-4-hydroxy-n-butyl-1-amino)phenyl pyrazol-3-in-5-one-4-carbonylamino)-2-phenyl]acetamido penicillanic acid.

* * * * *